United States Patent
Gorn et al.

(10) Patent No.: US 11,628,284 B2
(45) Date of Patent: Apr. 18, 2023

(54) DRAINAGE CATHETER SYSTEM INCLUDING A HUB

(71) Applicant: EM Device Lab, Inc., Austin, TX (US)

(72) Inventors: Michael Gorn, Austin, TX (US); Gary McGregor, Pflugerville, TX (US)

(73) Assignee: EM DEVICE LAB, INC., Austin, TX (US)

( * ) Notice: Subject to any disclaimer, the term of this patent is extended or adjusted under 35 U.S.C. 154(b) by 415 days.

(21) Appl. No.: 16/890,133

(22) Filed: Jun. 2, 2020

(65) Prior Publication Data

US 2020/0289802 A1 Sep. 17, 2020

Related U.S. Application Data

(63) Continuation of application No. 15/383,062, filed on Dec. 19, 2016, now Pat. No. 10,814,110.
(Continued)

(51) Int. Cl.
*A61B 17/04* (2006.01)
*A61M 27/00* (2006.01)
(Continued)

(52) U.S. Cl.
CPC .......... *A61M 27/00* (2013.01); *A61B 17/0487* (2013.01); *A61B 17/06066* (2013.01);
(Continued)

(58) Field of Classification Search
CPC .......... A61B 17/0487; A61B 17/06066; A61B 17/3415; A61B 2017/00292; A61B 2017/00473; A61B 2017/00641; A61B 2017/00876; A61B 2017/00946; A61B 2017/0461; A61B 2017/06071; A61B 2017/0608; A61B 2017/22067;
(Continued)

(56) References Cited

U.S. PATENT DOCUMENTS 383,733 A 5/1888 Jenkins
1,981,651 A 11/1934 Logan
(Continued)

FOREIGN PATENT DOCUMENTS

CA 3038516 A1 8/2017
EP 3205368 8/2017
(Continued)

OTHER PUBLICATIONS

Chinese Patent Office, Office Action dated Oct. 20, 2022 in Chinese Patent Application No. 202080019047.4 (12 pages).
(Continued)

*Primary Examiner* — Kai H Weng
(74) *Attorney, Agent, or Firm* — Trop, Pruner & Hu, P.C.

(57) ABSTRACT

A drainage device may include a catheter including a proximal end and a distal end. The drainage device may further include a hub coupled to the proximal end of the catheter. The hub may include a fastener element configured to secure the distal end of the catheter. In some aspects, the fastener element may be a hinged element. In some aspects, the drainage device may further include a puncture element including a tip and an expander portion. In still other aspects, the puncture element may also include an attachment portion.

12 Claims, 19 Drawing Sheets

Related U.S. Application Data

(60) Provisional application No. 62/383,370, filed on Sep. 2, 2016, provisional application No. 62/292,782, filed on Feb. 8, 2016.

(51) Int. Cl.
*A61B 17/34* (2006.01)
*A61B 17/06* (2006.01)
*A61M 25/00* (2006.01)
A61B 17/00 (2006.01)
A61B 17/22 (2006.01)

(52) U.S. Cl.
CPC ....... *A61B 17/3415* (2013.01); *A61M 25/007* (2013.01); *A61M 25/0097* (2013.01); *A61B 2017/00292* (2013.01); *A61B 2017/00473* (2013.01); *A61B 2017/00641* (2013.01); *A61B 2017/00876* (2013.01); *A61B 2017/00946* (2013.01); *A61B 2017/0461* (2013.01); *A61B 2017/0608* (2013.01); *A61B 2017/06071* (2013.01); *A61B 2017/22067* (2013.01); *A61B 2217/007* (2013.01)

(58) Field of Classification Search
CPC .......... A61B 2217/007; A61M 25/007; A61M 25/0097; A61M 27/00
See application file for complete search history.

(56) References Cited

U.S. PATENT DOCUMENTS

| | | |
|---|---|---|
| 2,841,150 A | 7/1958 | Riall |
| 2,910,983 A | 11/1959 | James |
| 3,611,551 A | 10/1971 | Shave et al. |
| 3,799,169 A | 3/1974 | Beroff |
| 3,875,946 A | 4/1975 | Duncan |
| 3,892,240 A | 7/1975 | Park |
| 4,418,875 A | 12/1983 | Brine |
| 4,524,771 A | 6/1985 | McGregor et al. |
| 4,723,948 A | 2/1988 | Clark et al. |
| 4,799,483 A | 1/1989 | Kraff |
| 4,932,963 A | 6/1990 | Ritter et al. |
| 5,002,528 A | 3/1991 | Palestrant |
| 5,080,270 A | 1/1992 | Kai |
| 5,089,011 A | 2/1992 | Korthoff |
| 5,354,282 A | 10/1994 | Bierman |
| 5,429,616 A | 7/1995 | Schaffer |
| 5,830,183 A | 11/1998 | Krieger |
| 6,290,691 B1 | 9/2001 | Krieger |
| 6,893,424 B2 | 5/2005 | Shchervinsky |
| 7,897,090 B2 | 3/2011 | Gudladt |
| 8,079,991 B2 | 12/2011 | Watson |
| 9,518,667 B2 | 12/2016 | Ramos et al. |
| 2002/0004650 A1 | 1/2002 | Kuracina et al. |
| 2003/0120216 A1* | 6/2003 | Bouphavichith ... A61J 15/0026 604/178 |
| 2004/0006311 A1 | 1/2004 | Shchervinsky |
| 2004/0243146 A1 | 12/2004 | Chesbrough et al. |
| 2004/0245613 A1 | 12/2004 | Lee |
| 2005/0240147 A1 | 10/2005 | Makower et al. |
| 2007/0100296 A1 | 5/2007 | Hwang |
| 2008/0116218 A1 | 5/2008 | Iacona |
| 2008/0312578 A1 | 12/2008 | DeFonzo et al. |
| 2011/0125133 A1 | 5/2011 | Aggerholm et al. |
| 2012/0245613 A1 | 9/2012 | Yee |
| 2013/0274686 A1 | 10/2013 | Ziebol et al. |
| 2013/0274719 A1 | 10/2013 | Berkey et al. |
| 2014/0060655 A1 | 3/2014 | Ramos et al. |
| 2014/0275777 A1 | 9/2014 | Gunday et al. |
| 2014/0276655 A1 | 9/2014 | Murray et al. |
| 2015/0141962 A1 | 5/2015 | Collins et al. |
| 2015/0250460 A1 | 9/2015 | Horeman et al. |
| 2017/0224967 A1 | 8/2017 | Gorn et al. |
| 2020/0001057 A1 | 1/2020 | Gorn et al. |

FOREIGN PATENT DOCUMENTS

| | | |
|---|---|---|
| WO | 9966975 | 12/1999 |
| WO | WO 2008/021596 | 2/2008 |
| WO | WO 2010/062796 | 6/2010 |
| WO | WO2013059204 | 4/2013 |

OTHER PUBLICATIONS

Australian Patent Office, Australian Examination Report dated Feb. 6, 2020 in Australian patent application No. 2017218392, 4 pages total.
Written Opinion and Search Report, PCT/US17/15571, dated May 18, 2017, 11 pages.
International Searching Authority, "Notification of Transmittal of the International Search Report and the Written Opinion of the International Searching Authority," dated Jun. 30, 2020, in International application No. PCT/US2020/021338.
European Patent Office, Office Action dated Sep. 19, 2022 in European Patent Application No. 20766827.8 (6 pages).
European Patent Office, Supplementary European Search Report dated Jun. 26, 2020 in European patent application No. EP 17 75 0568, 13 pages total.
United States Patent Office, Notice of Allowance dated Oct. 20, 2022 in U.S. Appl. No. 16/293,932 (13 pages).

* cited by examiner

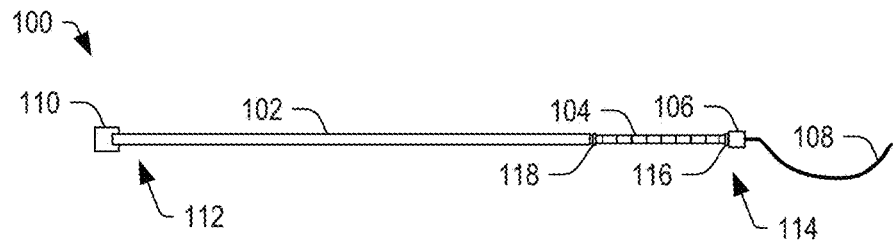
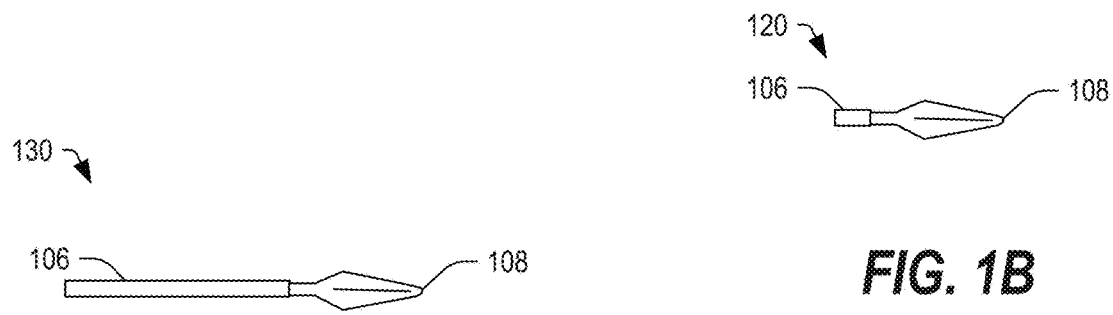
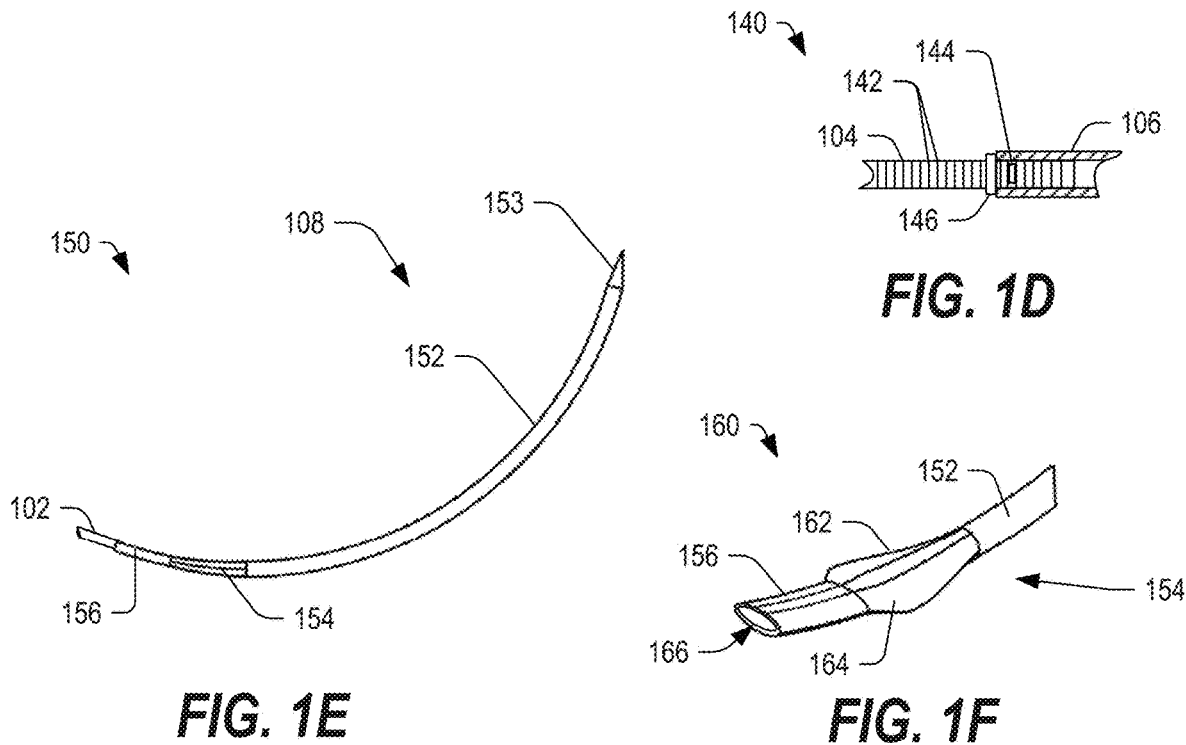

DRAINAGE CATHETER SYSTEM INCLUDING A HUB

CROSS-REFERENCE TO RELATED APPLICATION(S)

The present application is a continuation of U.S. patent application Ser. No. 15/383,062, filed Dec. 19, 2016, which: (a) claims priority to and is a nonprovisional of U.S. Provisional Patent Application No. 62/292,782 filed on Feb. 8, 2016 and entitled "Drainage Catheter Including a Hub", and (b) claims priority to and is a nonprovisional of U.S. Provisional Patent Application No. 62/383,370 filed on Sep. 2, 2016 and entitled "Drainage Catheter System Including a Hub". The content of each of the above applications is hereby incorporated by reference.

FIELD

The present disclosure is generally related to treating infections, and more particularly to devices and methods configured to treat cutaneous and oral abscesses.

BACKGROUND

Surgical drains are used in a wide variety of different surgical procedures. Typically, such drains are used to drain fluid from a surgical area. Some examples where such drains are used may include plastic surgery, breast surgery (to prevent collection of blood, lymph fluid, or both), orthopedic procedures, chest drainage, infected cysts, pancreatic surgery (to drain secretions), biliary surgery, thyroid surgery, neurosurgery (to remediate risk of intracranial pressure), urinary catheters, nasogastric tubes, and other procedures.

One class of such surgical drains are used on patients with cutaneous and oral abscesses, or collections of pus, hematomas, seromas or any other fluids requiring drainage. For example, abscesses can form anywhere in the body, from a superficial skin (subcutaneous) abscess to deep abscesses in muscle, organs, or body cavities. Treatment of such abscesses typically involves draining the accumulated fluid (such as pus) to resolve the infection or cause of the abscess and to facilitate recovery. One class of such surgical drains may require the patient or a care giver to adjust the drain to reopen clogged drainage paths to facilitate drainage.

The approach used to drain the accumulated fluid may depend on the size and location of the abscess. For subcutaneous abscesses, treatment typically includes creating an incision through the layers of the skin into the abscess cavity using a scalpel, expressing fluid (e.g., pus) from the abscess, and optionally using a hemostat to explore the wound and to break up pockets or localized areas of hardened pus. In some instances, packing material (such as a strip of gauze) may be inserted into the abscess cavity to prevent skin closure and re-accumulation of fluid in the abscess and to enable continued drainage. In other instances, a drainage catheter may be inserted through the incision and into the abscess to facilitate drainage and optionally irrigation of the abscess cavity.

The approach to draining abscesses in the oral cavity typically includes incision through the mucosa to the abscess cavity using a scalpel, expressing fluid (e.g., pus) from the abscess, and optionally using a hemostat to explore the wound and to break up pockets or localized areas of hardened pus. In most instances, a small drain is sutured into the cavity of the abscess cavity to mucosal closure and re-accumulation of fluid in the abscess and to enable continued drainage.

SUMMARY

In some embodiments, the herein disclosed drainage device may include a catheter including a proximal end and a distal end. The drainage device may further include a hub coupled to the proximal end of the catheter. The hub may include a fastener element configured to secure the distal end of the catheter. In some aspects, the fastener element may be a hinged element. In some aspects, the drainage device may further include a puncture element.

In some embodiments, a drainage device may include a catheter having a proximal end and a distal end and may include a hinged fastener coupled to the proximal end of the catheter. The hinged fastener may be configured to close over a portion of the catheter near the distal end to form a loop.

In still other embodiments, a drainage device can include a catheter and a puncture element. The catheter can include a proximal end and a distal end. The puncture element may be coupled to the distal end of the catheter. Further, the puncture element can include a tip and an expander portion including one or more cutting edges to extend an opening formed by the tip. The puncture element may further include an attachment portion configured to couple to the distal end of the catheter. In some aspects, the drainage device may also include a hub coupled to the proximal end of the catheter, the hub including a fastener configured to secure the distal end of the catheter.

In certain embodiments, a practitioner may insert the distal end of a catheter into a first opening, though an abscess, and out of a second opening. The catheter may include a fastener coupled to a proximal end. The method may further include coupling the distal end of the catheter to the fastener to form a loop. In some aspects, the fastener may include a port or ports that can be accessed to deliver fluid into the catheter.

BRIEF DESCRIPTION OF THE DRAWINGS

FIG. 1A illustrates a diagram of a drainage catheter including a puncture element and a fastener, in accordance with certain embodiments of the present disclosure.

FIGS. 1B and 1C depict diagrams of a puncture element and an attachment mechanism, in accordance with certain embodiments of the present disclosure.

FIG. 1D depicts a diagram of a portion of the drainage catheter including an attachment mechanism of a puncture element and an attachment portion of a drainage catheter, in accordance with certain embodiments of the present disclosure.

FIG. 1E illustrates a catheter including an alternative embodiment of a puncture element, in accordance with certain embodiments of the present disclosure.

FIG. 1F depicts a portion of the puncture element of FIG. 1E.

In the following discussion, the same reference numbers are used in the various embodiments to indicate the same or similar elements.

DETAILED DESCRIPTION OF ILLUSTRATIVE EMBODIMENTS

Figure 2A:
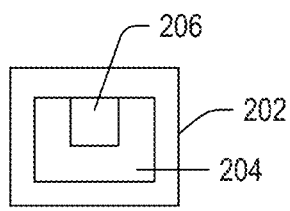
FIG. 2A depicts a diagram of an embodiment of a hub including an attachment mechanism, in accordance with certain embodiments of the present disclosure.

Embodiments of devices and methods are described below that are configured to facilitate abscess drainage. In an embodiment, an abscess drainage device may include a hub coupled to a catheter. The catheter may include a proximal end coupled to the hub, a drainage portion, and a distal end. In some embodiments, the distal end of the catheter may be coupled to a puncture element, which may include a needle portion that is curved, an expansion portion configured to enlarge an opening created by a tip of the needle portion, and an attachment portion configured to engage the catheter.

In some embodiments, the distal end of the catheter may include a fastening element configured to engage a fastener of the hub to form a loop. The fastening element can include at least one of a zip-tie, a cinch-lock, a clip, a latch, a knot, a magnet, a barbed or double-barbed attachment, an adhesive, a chemical bond, a weld, a double-hinge clamp, an intermediate material bond, a ratchet, a hook-and-eye fabric, a buckle, a carabiner, a spring-loaded clamp, a directional clamp, a swage, a tube lock, a push-to-connect tube fitting, a crimp fitting, a shark bite fitting, and a piece of tape.

In some embodiments, the hub may include a fluid port to receive an irrigation fluid, and the catheter may include a lumen extending through at least a portion of the catheter and including openings to deliver irrigation fluid from the lumen to a cutaneous abscess. Further, in some embodiments, the hub may include a second fluid port to receive a fluid under pressure (such as air) to inflate a balloon associated with the catheter. In this example, the catheter may include a second lumen extending between the second fluid port and the balloon.

In some embodiments, the fastener of the hub may be on an external surface of the hub or may extend through a portion of the hub that is separate from the fluid ports and lumen. In a particular implementation, the fastener may include a zip-tie fastener configured to engage a fastener portion (including ridges) at a distal end of the catheter. In still other embodiments, the fastener may include an elastic band configured to engage the hub and to secure the fastener portion to the hub. One possible example of a zip-tie implementation is described below with respect to FIG. 1A.

FIG. 1A depicts a diagram of a drainage catheter, generally indicated by reference number 100, including a puncture element and a fastener, in accordance with certain embodiments of the present disclosure. The drainage catheter 100 may include a hub 110 coupled to or integrated with a proximal end 112 of a catheter 102. The catheter 102 may include a fastener element 104 coupled to or integrally formed as part of a distal end 114 of the catheter 102 and configured to engage a fastener of the hub 110 to secure the catheter 102 in a loop configuration. The drainage catheter 100 may further include a puncture element 108, such as a needle or blade, which may be coupled to the fastener element 104 by a coupling mechanism 106. The coupling mechanism 106 may include a crimped feature of the puncture element 108, which may be configured to receive the distal end 114 of the catheter 102 and to be crimped to mechanically secure the distal end 114 to the puncture element 108. Further, in addition to crimping (or in lieu of crimping), the distal end 114 may be coupled to the puncture element 108 by an adhesive, by an adhesive and a mechanical crimp, by another type of connection, or any combination thereof.

In some embodiments, the fastener element 104 may include a plurality of ridges, which may be configured to engage a locking feature within the fastener of the hub 110. Further, the fastener element 104 may include a stopper 116, which may be a ridge that is larger than others of the ridges and which may be configured to provide an end stop to the coupling mechanism 106. In certain embodiments, the puncture element 108 may be integrated with the coupling mechanism 106. The drainage catheter 100 may be provided with the catheter 102 including the hub 110 and a plurality of puncture elements 108 from which a physician may select. In some embodiments, the catheter 102, the hub, and a plurality of puncture elements 108 may be provided as a kit, and the physician may select and assemble the elements based on the particular wound to be treated The physician may select a suitable puncture element 108 and may couple the puncture element 108 to the fastener element 104 by sliding the coupling mechanism 106 onto an end of the fastener element 104 and advancing the coupling mechanism 106 until it engages the stopper 116. In an alternative embodiment, the physician may slide the puncture element 108 over an end of the catheter 102 and crimp the puncture element 108 (such as with pliers) to grip the catheter 102. Other connections are also possible.

The physician may then advance the puncture element 108 through a first incision, through an abscess and out of a second incision. The puncture element 108 and the coupling mechanism 106 draw the catheter 102 along the path traversed by the puncture element 108, and the hub 110 may operate as a stopper to prevent the catheter 102 from being pulled out through the second incision.

Once the puncture element 108 exits the second incision and is pulled far enough to expose at least a portion of distal end 114 of the catheter 102, the physician may cut the fastener element 104 (or the catheter 102) to remove the puncture element 108. In some embodiments, the fastener element 104 may include a "cut area" having no ridges to facilitate cutting. Further, after the cut is made and the puncture element 108 is removed, a portion of the fastener element 104 including ridges may remain and may be configured to engage a fastener of the hub 110 to secure the distal end 114. The resulting configuration forms a catheter loop that extends into a first incision, through an abscess, and out from a second incision. The physician may pull on the loop to open the incision sufficiently to enable insertion of a portion of a hemostat, which the physician may move around in order to dislodge the collection of fluid within the abscess.

In some embodiments, the catheter 102 may be a silicone catheter, with or without the needle. The catheter 102 may be used as a drainage tool for a variety of different wounds. Further, the catheter 102 may be used to prevent infection in dirty wounds. These wounds may be cutaneous wounds from animal bites, injuries while swimming in lakes (fresh bodies of water), on dirt or road/asphalt, or from other sources. The catheter 102 may be inserted and formed into a loop, which can be sewn in, without (in any way) attaching the catheter to the skin of the patient. Such drainage without attachment is needed with a Penrose drain, which is a surgical device named for the American gynecologist Charles Bingham Penrose (who died in 1925) and which device is placed in a wound to drain fluid. Thus, the catheter 102 may be used in lieu of such a drain.

As discussed above, a collection of puncture elements 108 may be provided, which may include different sizes and shapes. In some embodiments, the curvature of the puncture elements 108 may also vary to facilitate puncturing of abscesses at different depths. In some embodiments, the puncture element 108 may be formed from a deformable material, such as a thin metal, which may be bent or otherwise formed to have a selected shape. Further, in some embodiments, the shape and size of the puncture element may remain consistent while the length of the coupling mechanism 106 may vary. In some embodiments, the coupling mechanism 106 may be configured to be deformed (e.g., shaped, bent, curved, etc.) and to retain the adjusted shape to enable a physician to adjust a shape (e.g., curvature) of the coupling mechanism 106 according to a selected application. In some embodiments, both the shape of the puncture element 108 and the length of the coupling mechanism 106 may be selected. Other embodiments are also possible.

In some embodiments, the hub 110 may include a fastener (such as fastener 202 in FIG. 2), which may be configured to secure the distal end 114 of the catheter 102 to the hub 110. While the illustrated example of the fastener element 104 includes a side view of a zip-tie type of fastener, other embodiments are also possible. In an example, the fastener element 104 can include a zip-tie, a cinch-lock, a clip, a latch, a knot, a magnet, a barbed or double-barbed attachment, an adhesive, a chemical bond, a weld, a double-hinge clamp, an intermediate material bond, a ratchet, a hook-and-eye fabric, a buckle, a carabiner, a spring-loaded clamp, a directional clamp, a swage, a tube lock, a push-to-connect tube fitting, a crimp fitting, a shark bite fitting, and a piece of tape. In some examples, the fastener element 104 may be any device or element that can be configured to couple the distal end of the catheter 102 to the hub 110.

FIGS. 1B and 1C are diagrams of devices 120 and 130 including a puncture element 108 and an attachment mechanism 106, in accordance with certain embodiments of the present disclosure. In FIG. 1B, the device 120 includes the puncture element 108 and a coupling mechanism 106. In the illustrated example, the coupling mechanism 106 is shorter than the puncture element 108.

In FIG. 1C, the device 130 include a puncture element 108 and a coupling mechanism 106 that is longer than that of the device 120 in FIG. 1B. The longer coupling mechanism 106 provides versatility to allow a physician to shape the coupling mechanism 106 along its length, if necessary. In some embodiments, the coupling mechanism 106 may be preconfigured with a selected shape or curvature.

While the embodiments shown in FIGS. 1A-1C depict a single puncture element 108, other puncture elements (such as that in FIG. 1E) having different shapes and sizes are also possible. Further, as mentioned above, in some embodiments, the puncture elements 108 may be selected from a plurality of possible puncture elements and may be coupled to the fastener element 104 by the coupling mechanism 106. One possible example of the coupling mechanism is described below with respect to FIG. 1D.

FIG. 1D depicts a diagram of a portion 140 of the drainage catheter 100 including a coupling mechanism 106 of a puncture element 108 and an attachment portion of a drainage catheter 102, in accordance with certain embodiments of the present disclosure. The coupling mechanism 106 may include a locking mechanism 144 configured to engage ridges 142 of the fastener element 104. The coupling mechanism 106 may be advanced onto the fastener element 104 until the coupling mechanism 106 engages the stopper 146. Other embodiments are also possible.

FIG. 1E illustrates a catheter 150 including an alternative embodiment of a puncture element (generally indicated at 108), in accordance with certain embodiments of the present disclosure. In the illustrated example, the puncture element 108 includes a first portion 152 having an arcuate or curved shape configured to draw the catheter 102 into, through and out from a wound. Further, the first portion 152 may include a tip or point 153 at its distal end that may be configured to puncture through layers of skin and cutaneous tissue as well as through a lesion. Further, the first portion 152 may be tapered along at least a portion of its length.

The puncture element 108 may include a second portion (or expander portion) 154, which may include one or more cutting edges configured to widen an opening created by the tip or point 153 to facilitate drainage of the lesion. In the illustrated example, the second portion 154 may include a cylindrical body corresponding to an outside diameter of the first portion 152 and including wings (or blades or edges) that may stick out from the surface of the cylindrical body to widen the opening created by the first portion 152. In a particular example, the catheter device 150 may include a puncture element 108 that includes an elongate, curved needle portion 152 with a puncture tip 153 that can be advanced through layers of skin and cutaneous tissue as well as through a lesion. In some embodiments, the cutting portion may be spaced apart from the puncture tip 153 by a pre-determined distance. In a particular example, the cutting portion or second portion 154 may be positioned along the length of the curved needle portion (first portion) 152 such that more than half of the needle portion 152 will have passed through the skin and cutaneous tissue before the cutting portion 154 begins to expand the opening created by the needle portion 152.

In some examples, the cutting portion 154 can include wings or blades that may be sharp along distal edges 162 and may be blunt or rounded along proximal edges 164 (as shown in FIG. 1F), making it possible to advance the puncture element 108 through the tissue and through the wound in a direction of the tip or point 133, widening the opening by cutting with the distal edges 162. Further, because the proximal edges 164 are blunt or dull, the puncture element 108 may be moved or pulled back toward the catheter 102 to break up solid portions of the fluid build-up to further facilitate drainage. In some embodiments, the cutting portion 154 may be formed by adding additional material (such as a metallic sleeve that can be slid over an outside diameter of a needle) and by applying pressure to deform at least the metallic sleeve at a localized portion of the needle 152.

The puncture element 108 may include a third portion (attachment portion) 156, which may have a substantially cylindrical shape with an opening (opening 166 in FIG. 1F). In some embodiments, the catheter 102 may fit into the opening to couple the catheter 102 to the puncture element 108. The interior surface of the third portion 156 that may be sized to receive the catheter 102 may include hooks or barbs or may be crimped or any combination thereof to mechanically secure the catheter 102 to the third portion 156. In some embodiments, an adhesive may be included within the opening 166 to further secure the catheter 102. In some embodiments, a profile of the third portion 156 is smaller than the profile of the second portion 154, but may be larger than a profile of the first portion 152.

FIG. 1F depicts a portion 160 of the puncture element 108 of FIG. 1E. The distal edges 162 of the second portion 154 may extend out from a cylindrical body portion to form a cutting edge. Further, the proximal edges 164 of the second portion 154 may be rounded or blunt and may curve toward the third portion 156.

In some embodiments, the third portion 156 may include an attachment feature configured to couple the puncture element 108 to the catheter 102. In the illustrated example, the third portion 156 may include a lumen or opening 166 sized to receive and secure an end of the catheter 102. In one possible implementation, the interior surface of the opening 166 may include an adhesive, one or more hooks, a ridge, another element or feature, or any combination thereof to mechanically secure the catheter 102 to the third portion 156. In an alternative embodiment, the third portion 156 may include an opening (such as an eye of a needle) through which the catheter 102 may be fed to secure the catheter 102 to the puncture element 108. Other embodiments are also possible.

FIG. 2A depicts a diagram of an embodiment of a hub 110 including an attachment mechanism, in accordance with certain embodiments of the present disclosure. The hub 110 includes a fastener 202 defining an opening 204 through which a fastener element 104 may be advanced. The fastener 202 may include a locking element 206 within the opening and configured to engage ridges on the fastening element 104 to secure the distal end of the catheter 102.

In certain embodiments, the fastener 202 may be coupled to an exterior surface of the hub 110. In other embodiments, the fastener 202 may be integrally formed within the hub 110.

In some embodiments, the fastener element 104 may include sidewalls that may be configured to engage sides of the locking element 206. One possible embodiment of a fastener element 104 is described below with respect to FIG. 2B.

Figure 2B:
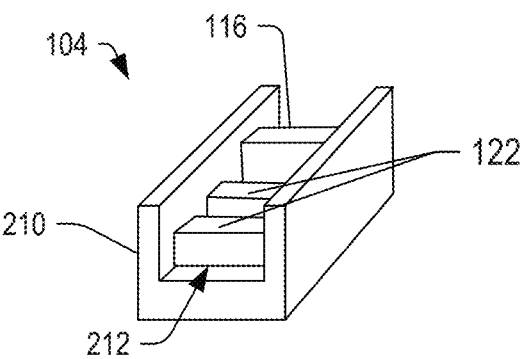
FIG. 2B depicts a diagram of an embodiment of an attachment portion of a drainage catheter, in accordance with certain embodiments of the present disclosure.

FIG. 2B depicts a diagram of an embodiment of an attachment portion of a drainage catheter, in accordance with certain embodiments of the present disclosure. The fastener element 104 may include sidewalls 210 defining a channel 212 that includes ridges 122 and the stopper 116. The sidewalls 210 may engage the sides of the locking element 206. Further, in the illustrated example, the stopper 116 is larger than the ridges 122 to provide a stop for the connection mechanism 106. Further, in some embodiments, a second stopper 116 may be provided to engage a locking element 206 of a fastener of the hub 110 to prevent the catheter 102 from being pulled too far. Other embodiments are also possible.

Figure 2C:
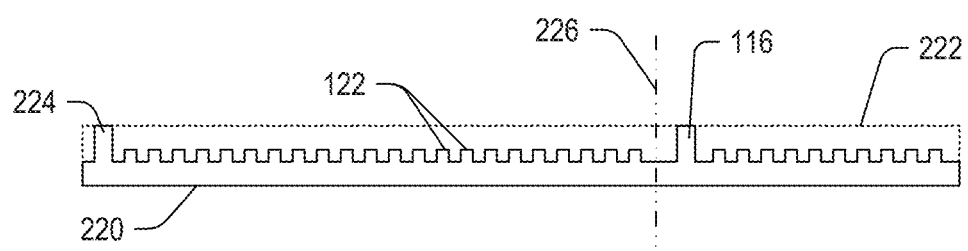
FIG. 2C illustrates a side view of an embodiment of the attachment portion of the drainage catheter of FIG. 2B, in accordance with certain embodiments of the present disclosure.

FIG. 2C is a side view of an embodiment of the attachment portion of the drainage catheter of FIG. 2B, in accordance with certain embodiments of the present disclosure. The fastener element 104 may include a substrate 220 and a plurality of ridges 122 formed thereon. The sidewalls 222 are shown in phantom. In an embodiment, the sidewalls 222 may be an example of the sidewall 210 in FIG. 2B. Further, a stopper 116 extends from the base 220 to the same height as the sidewalls 222, while the ridges 122 do not extend to the height of the sidewalls 222. The stopper 116 may be configured to engage the coupling mechanism 106 associated with the puncture element 108.

The fastener element 104 may include a second stopper 224, which may be configured to engage a fastener associated with a hub 110 to prevent the fastener element 104 from being pulled past the locking mechanism of the fastener. Further, the fastener element 104 may include a cutting area having no ridges 122 to facilitate removal of the puncture element 108. In the illustrated example, a physician may cut through the fastener element 104 in the cutting area by cutting along dashed line 226. By cutting in this area, the fastener element 104 is left with a portion that includes ridges 104, even after cutting, which ridges may engage a locking mechanism of the fastener of the hub 110.

While the stoppers 116 and 224 are depicted as extending from the substrate 220 to a height of the sidewalls 222, the stoppers 116 and 224 may be sized differently. In some embodiments, the stoppers 116 and 224 may have the same height as the ridges 122, but may extend horizontally beyond the exterior surface of the sidewalls 222, of the substrate 220, or both. In some embodiments, the stoppers 116 and 224 may be thicker along a longitudinal axis of the fastener element 104. The stoppers 116 and 224 may be configured to prevent advancing of the fastener element 104 past a connection structure. Other embodiments are also possible.

Figure 3:
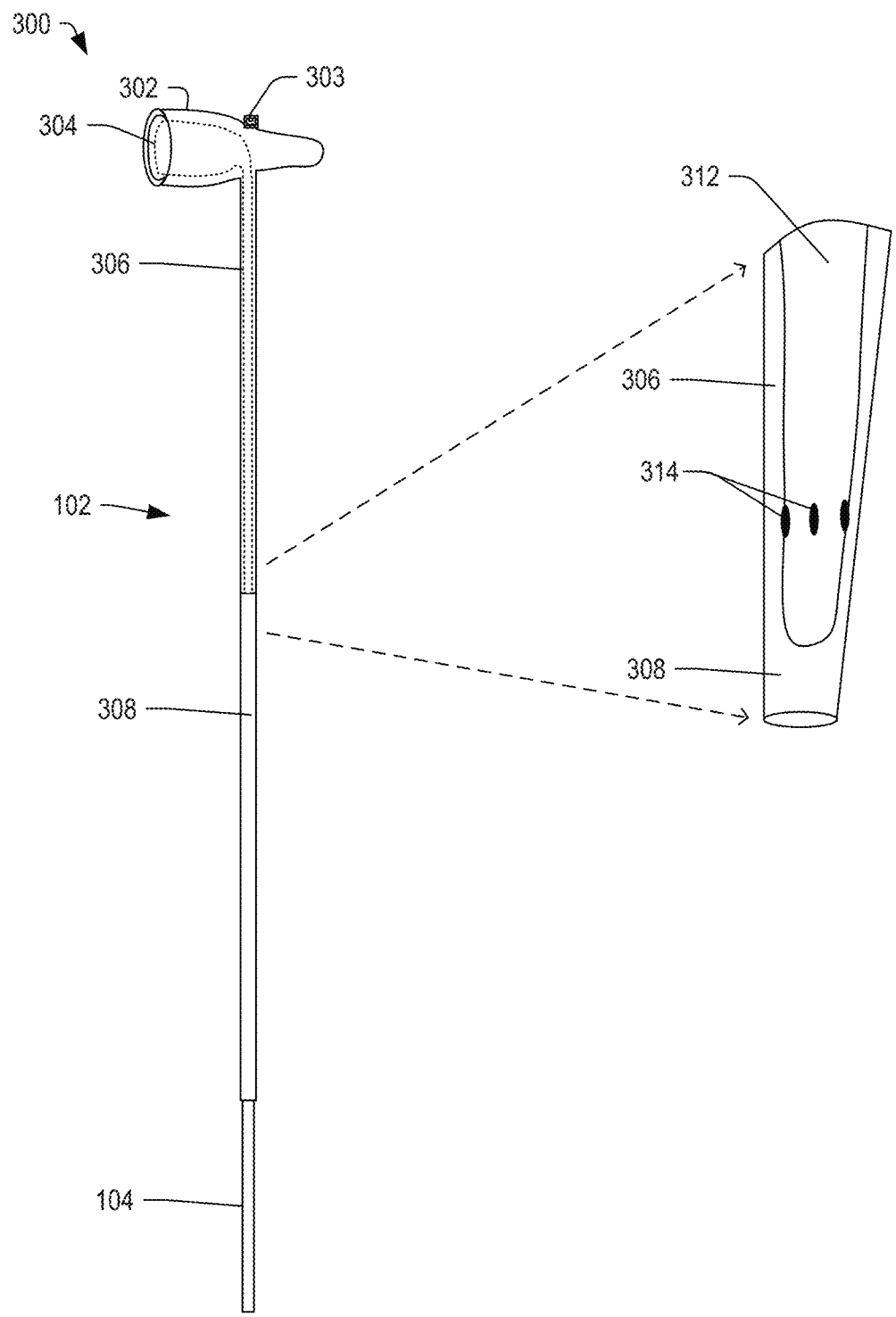
FIG. 3 depicts a diagram of an embodiment an abscess draining device including a hub with a fastener and including a port configured to receive an irrigation fluid, in accordance with certain embodiments of the present disclosure.

FIG. 3 depicts a diagram of an embodiment an abscess draining device 300 including a hub 302 with a fastener 303 and including a port 304 configured to receive an irrigation fluid, in accordance with certain embodiments of the present disclosure. The abscess draining device 300 may further include a catheter 102 including an irrigation portion 306 and a solid portion 308. The catheter 102 may further include a fastener element 104 coupled to or forming a distal end.

In the illustrated embodiment, the port 304 may be configured to receive a sterile irrigation fluid, such as saline, or another fluid. The port 304 may be coupled to a lumen 312 within the irrigation portion 306. Further, as shown in the expanded view, the lumen 312 extends within the irrigation portion 306 and is coupled to openings 314 to deliver the sterile irrigation fluid to the abscess. In the illustrated example, the openings 314 are shown in a row extending substantially transverse to a longitudinal axis of the lumen 312; however, other arrangements of the openings are also possible. Further, a physician can adjust the relative positioning of the openings by adjusting the abscess draining device 300 to irrigate a selected area.

In the illustrated example, a fastener 303 is coupled to an exterior surface of the hub 302. The fastener 303 may be an embodiment of the fastener 202 of FIG. 2. The fastener 303 may be configured to secure the distal end 114 of the catheter 102 to the hub 302. While the illustrated example of the fastener element 303 includes a front view of a zip-tie type of fastener, other embodiments are also possible. In an example, the fastener element 303 can include a zip-tie, a cinch-lock, a clip, a latch, a knot, a magnet, a barbed or double-barbed attachment, an adhesive, a chemical bond, a weld, a double-hinge clamp, an intermediate material bond, a ratchet, a hook-and-eye fabric, a buckle, a carabiner, a spring-loaded clamp, a directional clamp, a swage, a tube lock, a push-to-connect tube fitting, a crimp fitting, a shark bite fitting, and a piece of tape. In some examples, the fastener element 303 may be any device or element that can be configured to couple the distal end of the catheter 102 to the hub 302.

Further, the hub 302 may be an embodiment of the hub 110 of FIGS. 1A-2A. The fastener 303 may be configured to receive and secure a fastener element 104. In other embodiments, the fastener 303 may be integrated within the hub 302. One possible example of an integrated fastener is described below with respect to FIG. 4.

Figure 4:
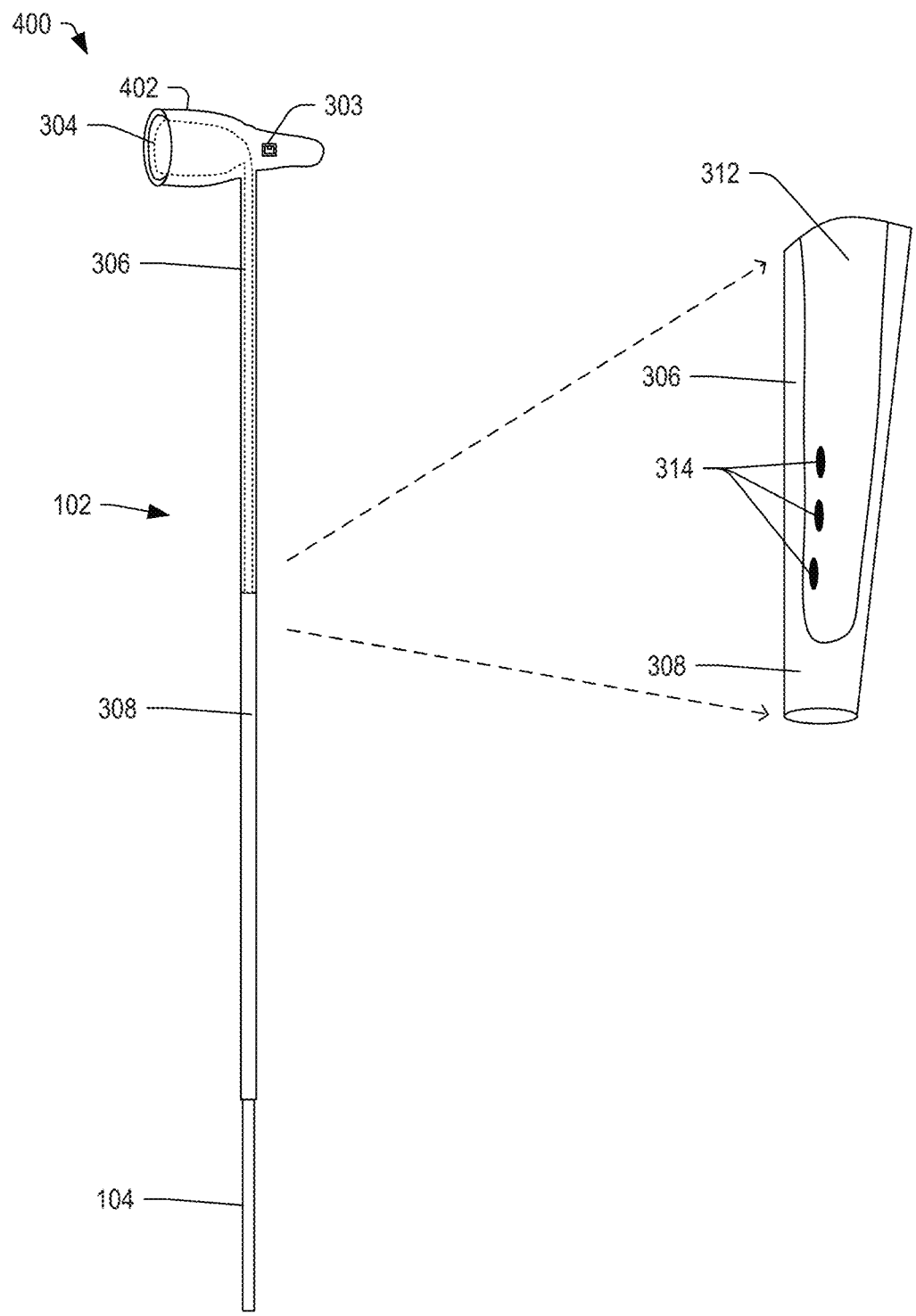
FIG. 4 depicts a diagram of an embodiment an abscess draining device including a hub with a fastener and including a port configured to receive an irrigation fluid, in accordance with certain embodiments of the present disclosure.

FIG. 4 depicts a diagram of an embodiment an abscess draining device 400 including a hub 402 with a fastener and including a port configured to receive an irrigation fluid, in accordance with certain embodiments of the present disclosure. The abscess draining device 400 includes all of the elements of the abscess draining device 300 of FIG. 3. The hub 402 is similar to the hub 302 of FIG. 3 except that the fastener 303 is integrated into the hub 402. In an example where the fastener 303 includes tape or a hook and eye fabric, one end may be coupled to the hub 402, while the other end hangs loose. Further, in some examples, such where the fastener is implemented as a clip, a portion of the clip may be integrated with the hub 402 and a portion may be configured to move relative to the hub 402 to implement a clasping or clamping action to secure the distal end 114. Other embodiments are also possible.

In some embodiments, the fastener 303 include an opening extending from one side of the hub 402 to the other so that the fastener element 104 may be pulled through the fastener 303 and out the other side. In other embodiments, the fastener 303 may include an opening that extends substantially parallel to the fluid opening 304, and the catheter 102 may also extend substantially parallel to a longitudinal axis of the fluid opening 304. Other embodiments are also possible.

Figure 5:
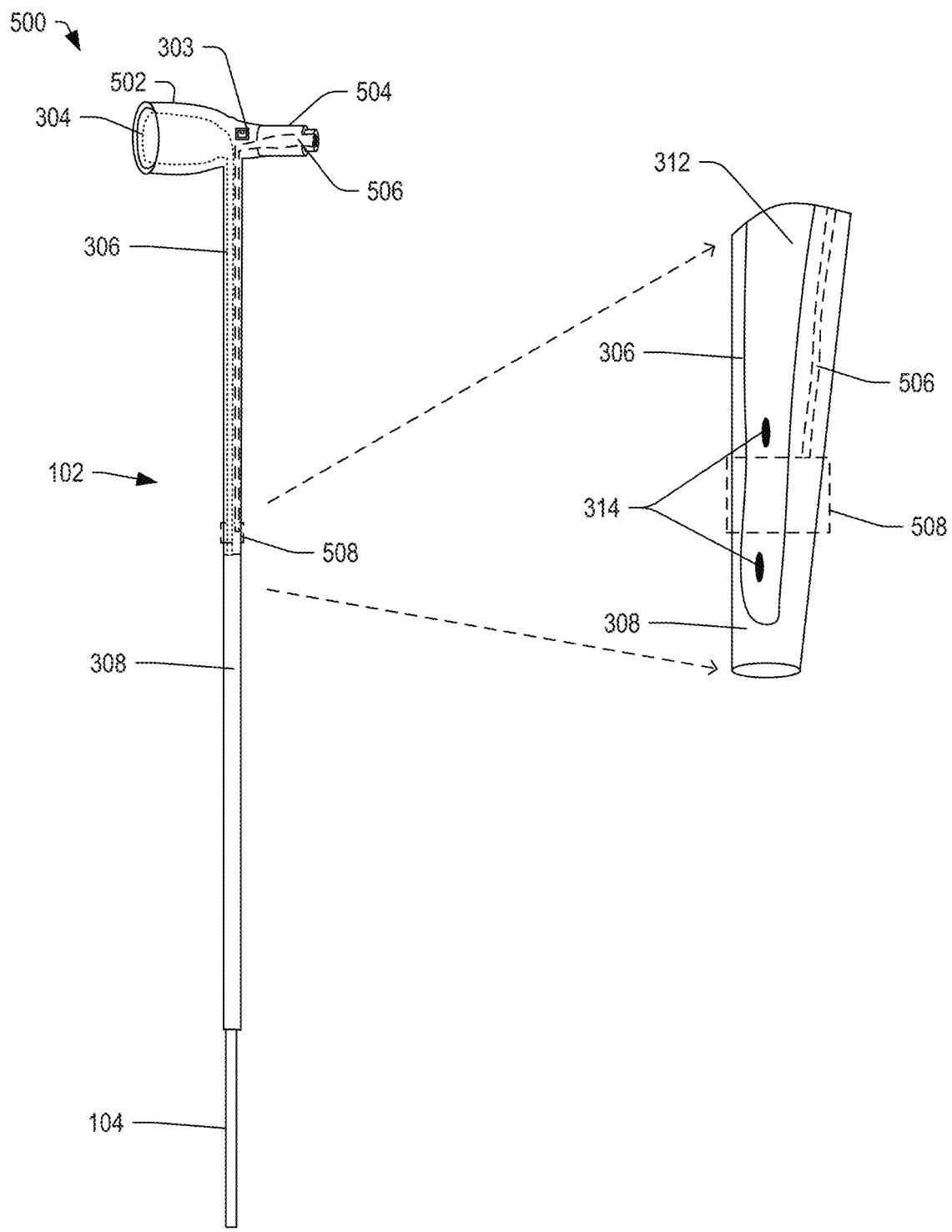
FIG. 5 depicts a diagram of an embodiment an abscess draining device including a hub with a fastener, a first port configured to receive an irrigation fluid, and a second port configured to receive a pressurized fluid, in accordance with certain embodiments of the present disclosure.

While the hub 402 described with respect to FIG. 4 includes a single fluid opening for receiving the irrigation fluid, it is also possible to include a second fluid opening configured to receive a pressurized fluid for inflating a balloon, for example. Further, when the catheter includes a balloon, the position of the irrigation openings may vary. One example of a dual port hub and a catheter including irrigation openings and a balloon is described below with respect to FIG. 5, FIG. 5 depicts a diagram of an embodiment an abscess draining device 500 including a hub 502 with a fastener 303, a first port configured to receive an irrigation fluid, and a second port configured to receive a pressurized fluid, in accordance with certain embodiments of the present disclosure. The hub 502 includes a fluid opening 304 for receiving an irrigation fluid. Further, the hub 502 may include a second port 504 coupled to a second lumen 506 that extends to a balloon 508 adjacent to the openings 314.

In the illustrated example, the pressurized fluid lumen 506 extends in parallel with the irrigation fluid lumen 312 to inflate the balloon 508 in an area adjacent to the openings 314. In some embodiments, the openings 314 may be on one side of the balloon 508. In other embodiments, the openings 314 may be on both sides of the balloon 508, as shown.

While only one opening 314 is shown, it should be appreciated that multiple openings may be provided.

Figure 6A:
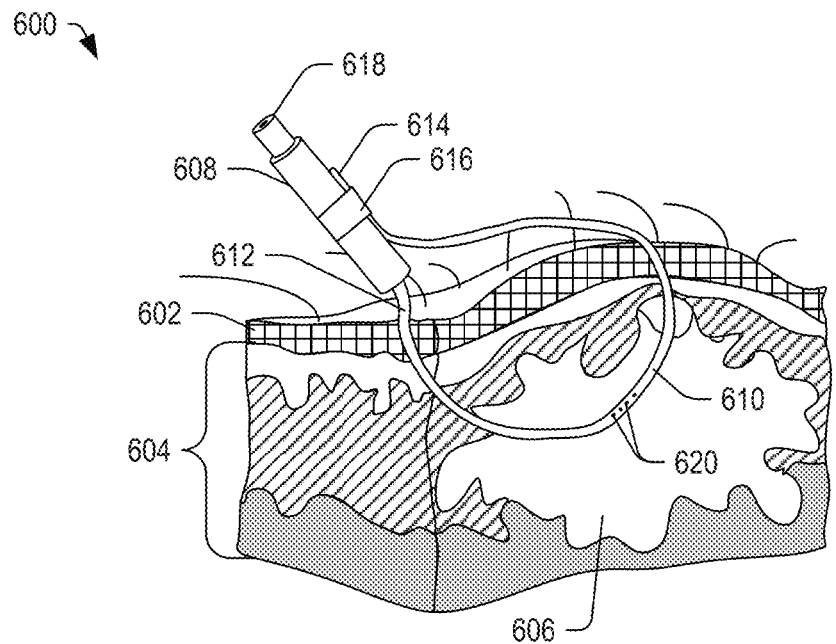
FIG. 6A depicts a diagram of an abscess draining device including a hub with a fastener and including a drainage catheter in situ, in accordance with certain embodiments of the present disclosure.

FIG. 6A depicts a diagram of an abscess draining device 600 including a hub 608 with a fastener 616 and including a drainage catheter 610 in situ, in accordance with certain embodiments of the present disclosure. The hub 608 may be coupled to a proximal end 612 of the catheter 610, and the fastener 616 may couple the distal end 614 of the catheter 610 to the hub 608. The catheter 610 may extend through a first incision through the epidermis 602 and optionally through one or more layers of the dermis 604, through an abscess 606, and out from a second incision. The hub 608 includes an irrigation fluid port 618 to receive a sterile irrigation fluid. The catheter 610 includes a lumen coupled to the irrigation port 618 and coupled to openings 620, which are positioned within the abscess 606, to deliver irrigation fluid into the abscess 606.

In the illustrated example, the fastener 616 may include an elastic portion configured to expand to receive the distal end 614 and to retract over the distal end to secure the catheter 610 to the hub 608. In another embodiment, the fastener 616 may include a hook and eye fabric configured to secure the distal end 614 to the hub 608. In an alternative embodiment, the fastener 616 may be replaced with a zip-tie fastener, a locking fastener, or another type of fastener. Alternatively, the fastener 616 could be implemented as any one of a zip-tie, a cinch-lock, a clip, a latch, a knot, a magnet, a barbed or double-barbed attachment, an adhesive, a chemical bond, a weld, a double-hinge clamp, an intermediate material bond, a ratchet, a buckle, a carabiner, a spring-loaded clamp, a directional clamp, a swage, a tube lock, a push-to-connect tube fitting, a crimp fitting, a shark bite fitting, and a piece of tape. In a particular example, the fastener could include a hinged element configured to close over the distal end 614 of the catheter 610.

In the illustrated embodiment of FIG. 6A, the drainage catheter 600 allows for introduction of irrigation fluid via the irrigation port 618 and the openings 620. In some embodiments, an additional port may be provided to allow for expansion of a balloon, for example. One possible embodiment of a drainage catheter including a hub having two ports is described below with respect to FIG. 6B.

Figure 6B:
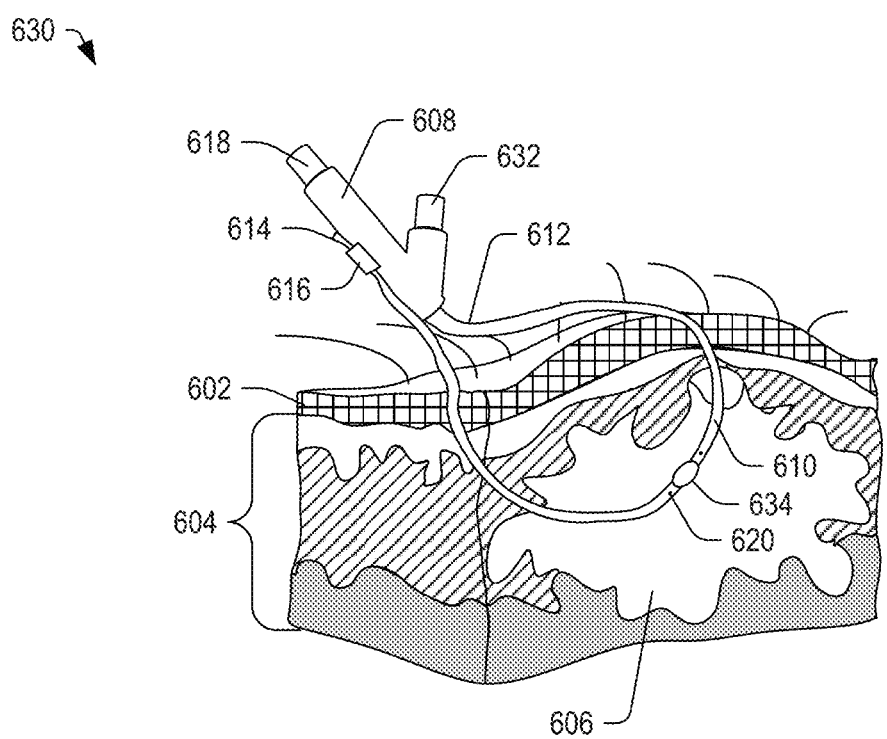
FIG. 6B depicts a diagram of an abscess draining device including a hub with a fastener and dual fluid ports and including a drainage catheter with an uninflated balloon element in situ, in accordance with certain embodiments of the present disclosure.

FIG. 6B depicts a diagram of an abscess draining device 630 including a hub 608 with a fastener 616 and dual fluid ports (618 and 632), and including a drainage catheter 610 in situ, in accordance with certain embodiments of the present disclosure. In the illustrated example, the hub 608 may be coupled to a proximal end 612 of the catheter 610 and to a distal end 614 of the catheter 610 via the fastener 616. In addition to the openings 620, the catheter 610 may also include a balloon 634, which may be coupled by a lumen to a pressurized fluid port 632. The catheter 610 may be positioned such that the openings 620 and the balloon 634 are positioned within the abscess 606.

In certain embodiments, the physician may apply irrigation fluid to the irrigation port 618 and may selectively apply pressurized fluid to the pressurized fluid port 632 to inflate the balloon 634. In some embodiments, a physician may inflate the balloon 634 by applying pressurized fluid to the pressurized fluid port 632 and then apply fluid to the irrigation fluid port 618. The balloon 634 may operate to confine the irrigation fluid in a particular region within the abscess 606. Other embodiments are also possible.

Figure 7:
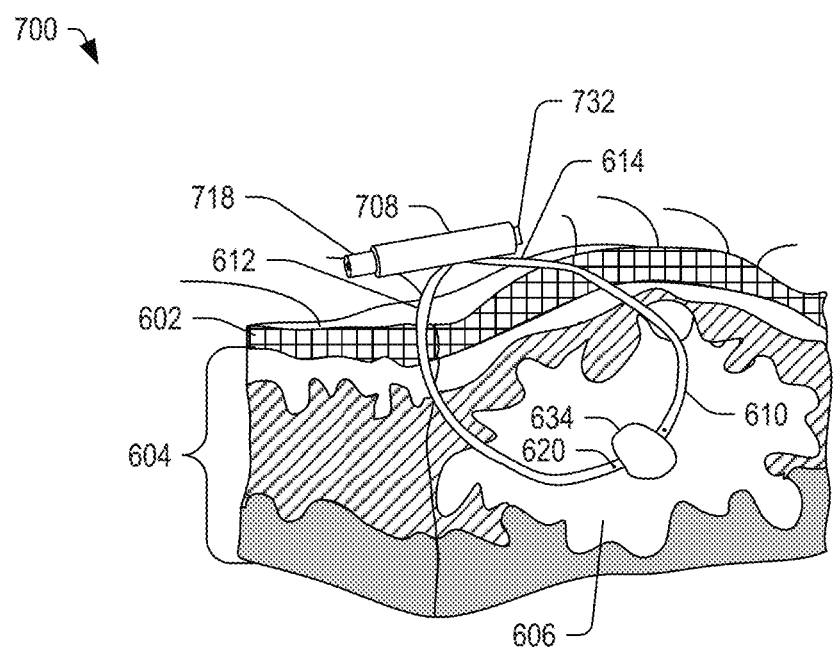
FIG. 7 depicts a diagram of an abscess draining device including a hub with a fastener and dual fluid ports and including a drainage catheter with an inflated balloon element in situ, in accordance with certain embodiments of the present disclosure.

FIG. 7 depicts a diagram of an abscess draining device 700 including a hub with a fastener and dual fluid ports and including a drainage catheter in situ, in accordance with certain embodiments of the present disclosure. The abscess draining device 700 may include all of the elements of the abscess draining device 630 of FIG. 6B, except that the irrigation port 618 and the pressurized fluid port 634 are arranged differently, reducing the overall size of the hub. Thus, hub 708 may be smaller than the hub 608 in FIG. 6B.

In the illustrated example, the irrigation port 718 and the pressurized fluid port 732 may be aligned on opposing ends of the hub 708. In some embodiments, the catheter 610 may extend substantially perpendicular to a longitudinal axis of the hub 708 and may the fastener may be part of the hub and may receive the distal end of the catheter 610 along a path that is substantially parallel to the direction in which the proximal end extends from the hub 708. In some embodiments, the catheter 710 may extend from the hub 708 substantially parallel to the longitudinal axis of the hub 708, and the distal end of the catheter 710 may also couple to a fastener of the hub 708 that extends parallel to the longitudinal axis of the hub 708. In such an embodiment, the hub 708 may lay flat with the flexible catheter loop.

As discussed above, the fastener may be implemented in a variety of different form factors and forms. In some embodiments, the fastener may be implemented as at least one of a zip-tie connector, a cinch-lock, a clip, a latch, a knot, a magnet, a barbed or double-barbed attachment, an adhesive, a chemical bond, a weld, a double-hinge clamp, an intermediate material bond, a ratchet, a hook-and-eye fabric, a buckle, a carabiner, a spring-loaded clamp, a directional clamp, a swage, a tube lock, a push-to-connect tube fitting, a crimp fitting, a shark bite fitting, and a piece of tape. Further, the fastener can be coupled to the hub 708 or integrated with the hub 708. Other embodiments are also possible.

Figure 8:
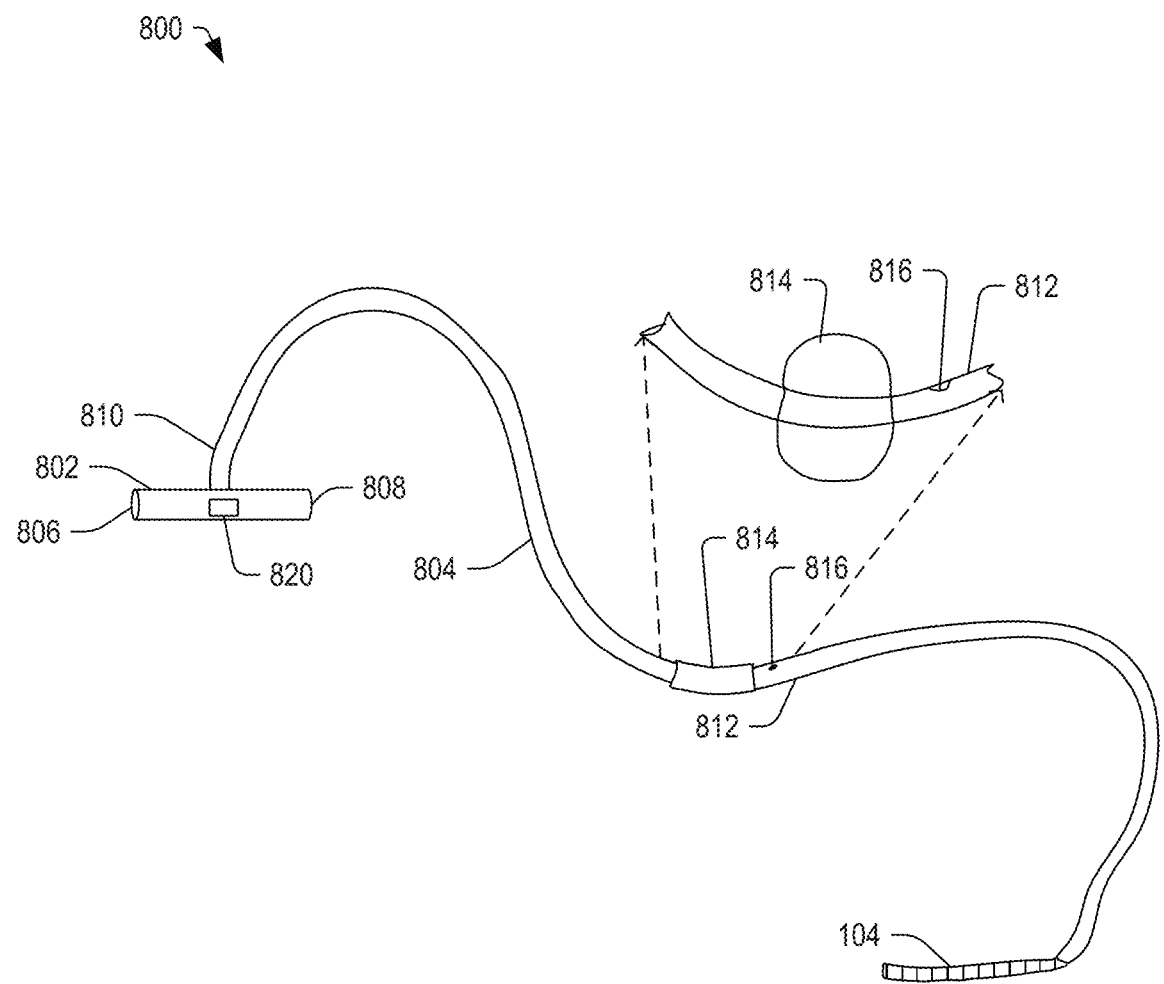
FIG. 8 depicts a diagram of an abscess draining device including a hub with a fastener and a drainage catheter including irrigation holes and a balloon, in accordance with certain embodiments of the present disclosure.

FIG. 8 depicts a diagram of an abscess draining device 800 including a hub 802 with a fastener 820 and a drainage catheter 804 including irrigation holes 816 and a balloon 814, in accordance with certain embodiments of the present disclosure. In the illustrated example, the hub 802 may include an irrigation port 806 and a pressurized fluid port 808. Further, the fastener 820 may be between the irrigation port 806 and the pressurized fluid port 808. The fastener 820 may be any of the types of fasteners described above with respect to FIGS. 1A-7.

Further, in the illustrated example, the proximal end 810 of the catheter 804 is coupled to the hub 802. Additionally, the balloon 814 and one or more openings 816 may positioned along a surface of the catheter 804 at a position 812 that may be located within an abscess. The catheter 804 may also include a fastener element 104 configured to engage the fastener 820.

In the expanded view, the balloon 814 may be inflated adjacent to the openings 816. In some embodiments, the relative position of the balloon 814 and the openings 816 within the abscess may be adjusted by selectively moving the drainage device within the wound. Further, in some embodiments, the balloon 814 may be inflated, deflated, and re-inflated to selectively apply pressure within the abscess. Additionally, irrigation fluid may be selectively provided to the irrigation port 806 to deliver irrigation fluid to the wound. Other embodiments are also possible.

Figure 9:
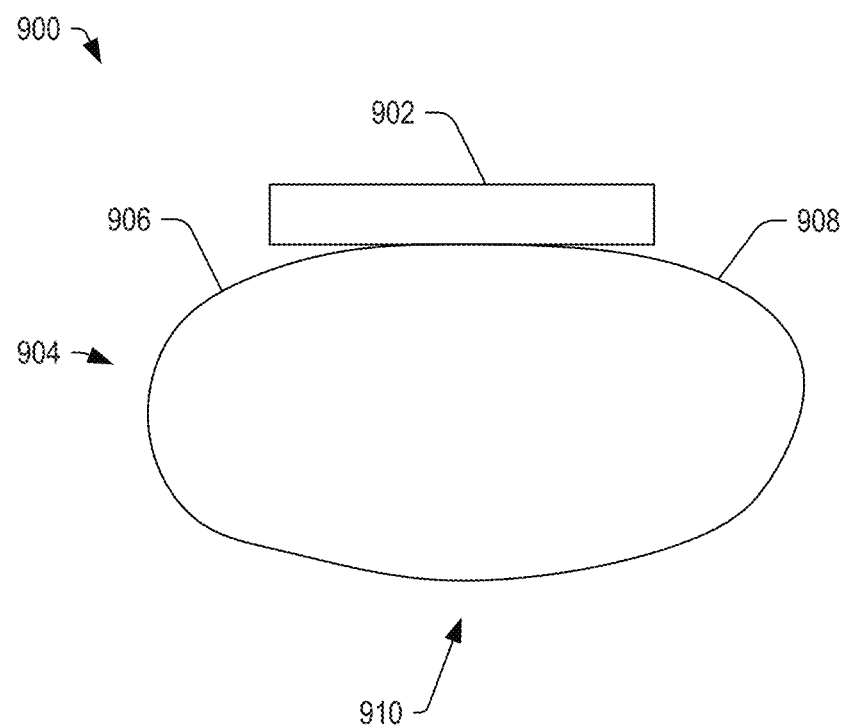
FIG. 9 depicts a block diagram of an abscess draining device including a hub with a fastener and a drainage catheter, in accordance with certain embodiments of the present disclosure.

FIG. 9 is a block diagram of an abscess draining device 900 including a hub 902 with a fastener and a drainage catheter 904, in accordance with certain embodiments of the present disclosure. In the illustrated example, the proximal end 906 and the distal end 908 of the catheter 904 extend from and return to the hub 902 along a plane that is parallel to a plane of the hub 902. The catheter 902 further includes a portion 910 that is intended to be located within an abscess or other treatment area for delivery of irrigation fluid, for inflation of a balloon, or both. Other embodiments are also possible.

In some embodiments, the fastener may be integrally formed as part of the hub 902, and the distal end of the catheter 904 may include a fastener element to engage the fastener. In some embodiments, the fastener element may extend through the hub 902 via the fastener. Other embodiments are also possible.

Figure 10:
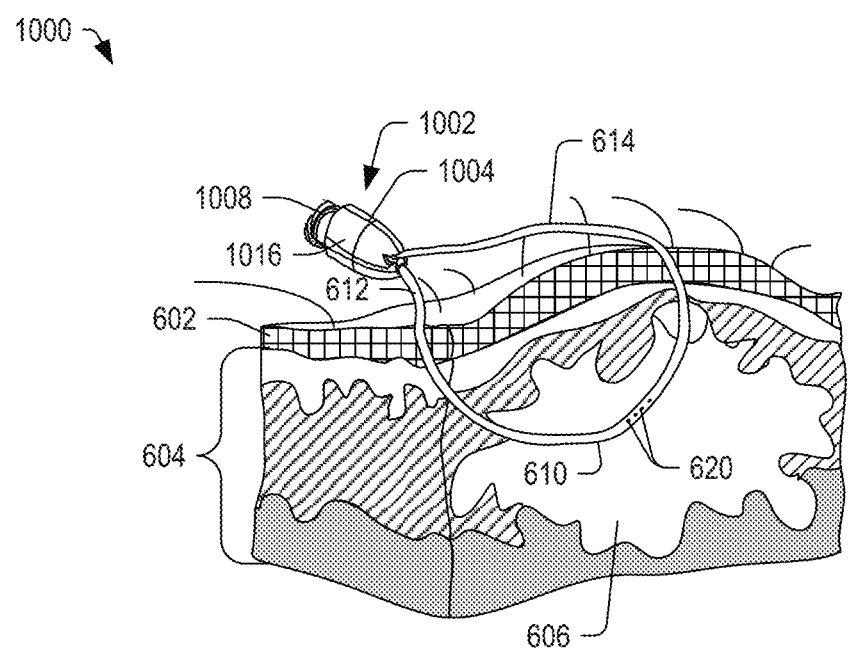
FIG. 10 depicts a diagram of a second abscess draining device in situ and including a hub with a fastener and a drainage catheter including irrigation holes, in accordance with certain embodiments of the present disclosure

FIG. 10 depicts a diagram of a second abscess draining device 1000 in situ and including a hub 1002 with a hinged fastener 1016 and a drainage catheter 610 including irrigation holes 620, in accordance with certain embodiments of the present disclosure. The hub 1002 may be coupled to a proximal end 612 of the catheter 610, which includes a distal end 614. The hinged fastener 1016 may be opened to receive the distal end 614 and may be closed to clamp down onto the distal end 614 (as shown). The hinged fastener 1016 may engage one or more catches to secure the hinged fastener 1016 in a closed position, applying a compressive force to the distal end 614 and securing the distal end 614 within the hub 1002.

Figure 11A:
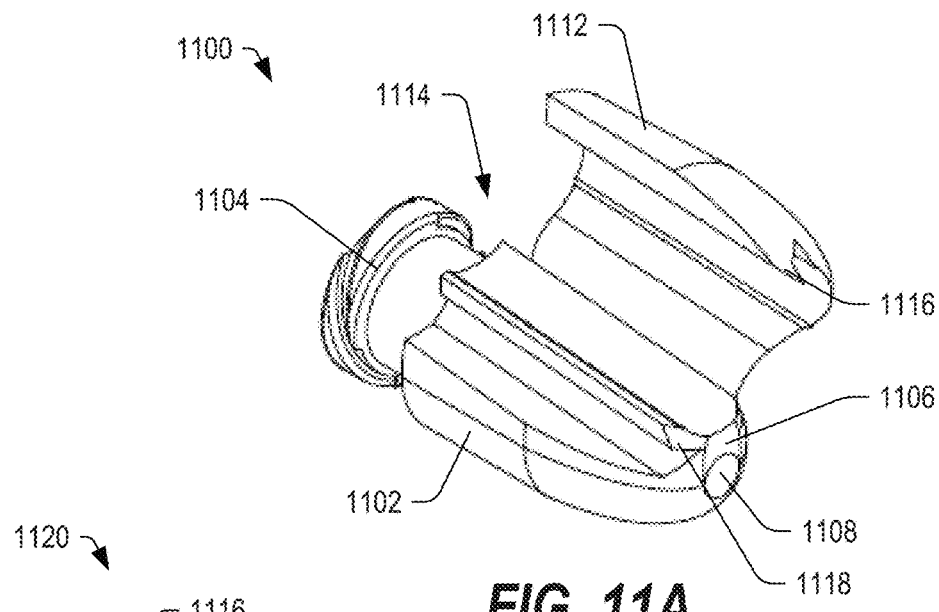
FIGS. 11A-11C depict perspective views of a second abscess draining device including a hub with a hinged fastener in an open position, in accordance with certain embodiments of the present disclosure.
Figure 11B:
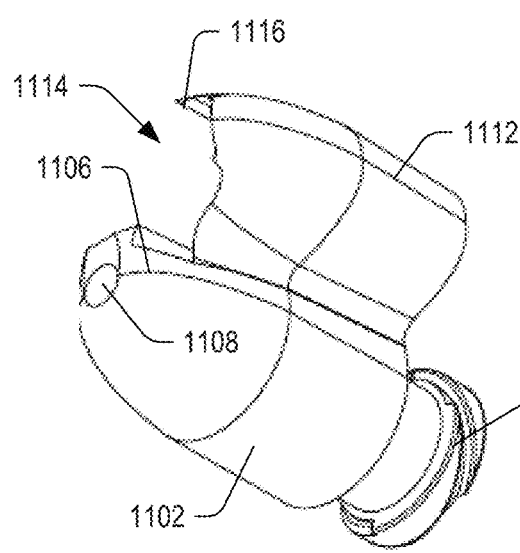
Figure 11C:
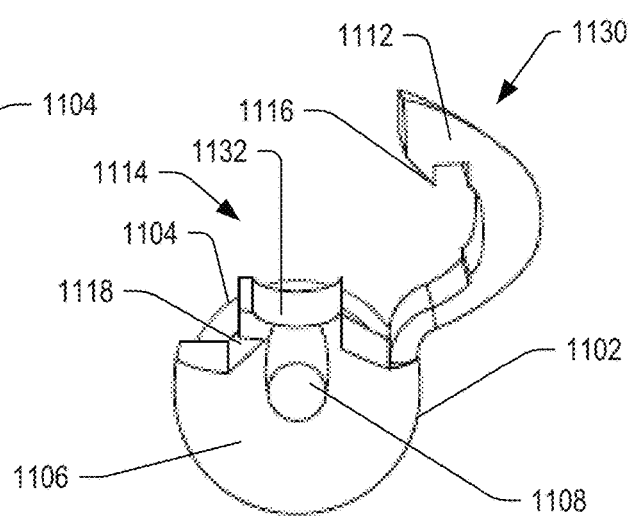

FIGS. 11A-11C depict perspective views of a second abscess draining device including a hub with a hinged fastener in an open position, in accordance with certain embodiments of the present disclosure. FIG. 11A shows a top perspective view 1100 of a hub 1102 including a proximal end 1104 and a distal end 1106. In some embodiments, the proximal end 1104 may be configured to operate as a port that may be sized to receive a syringe. A lumen may extend from the proximal end 1104 to the distal end 1106, as represented by the opening 1108.

The hub 1102 may include a hinged fastener 1112 coupled to the hub 1102 and defining an enclosure, generally indicated at 1114. The hinged fastener 1112 may further include a fastener element 1116 configured to engage a corresponding fastener element 1118 associated with the hub 1102 to close the hinged fastener 1112 over a distal end of the catheter tubing.

In certain embodiments, a proximal end of the catheter tubing may be coupled to the opening 1108 and the distal end of the catheter tubing may extend through the skin, through the abscess and back out from the skin. The distal end may be secured within the enclosure 1114 by placing the distal end within the enclosure 1114 and closing the hinged fastener 1112 such that the hinged fastener 1112 can secure the distal end of the catheter tubing to the hub 1102.

FIG. 11B depicts a bottom perspective view 1120 of the hub 1102. The proximal end 1104 may include a threaded portion configured to engage a corresponding structure of the syringe or other element.

FIG. 11C illustrates a front view 1130 of the hub 1102 taken from the perspective of the distal end 1106. As shown, the enclosure 1114 includes a ledge 1132 configured to receive the distal end of the tubing. The fastener element 1116 is configured to engage the corresponding fastener 1118 to close the hinged element 1112 over the distal end of the tubing.

Figure 12A:
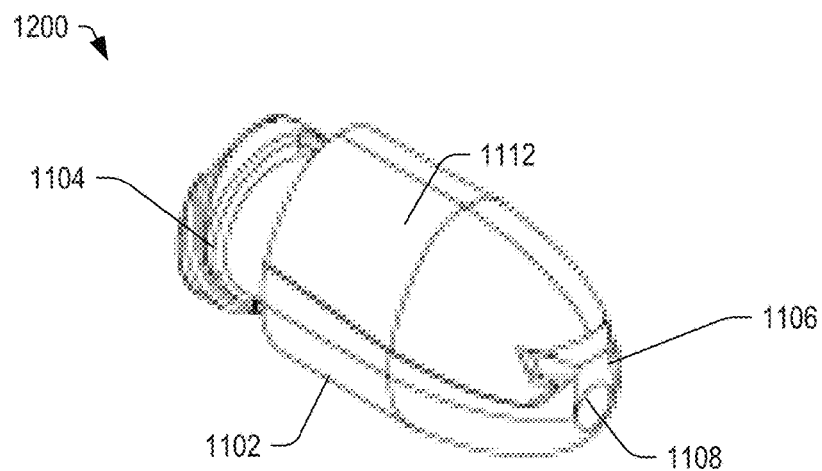
FIGS. 12A-12C depict perspective views of the second abscess draining device of FIGS. 11A-11C with the hinged fastener in a closed position, in accordance with certain embodiments of the present disclosure.
Figure 12B:
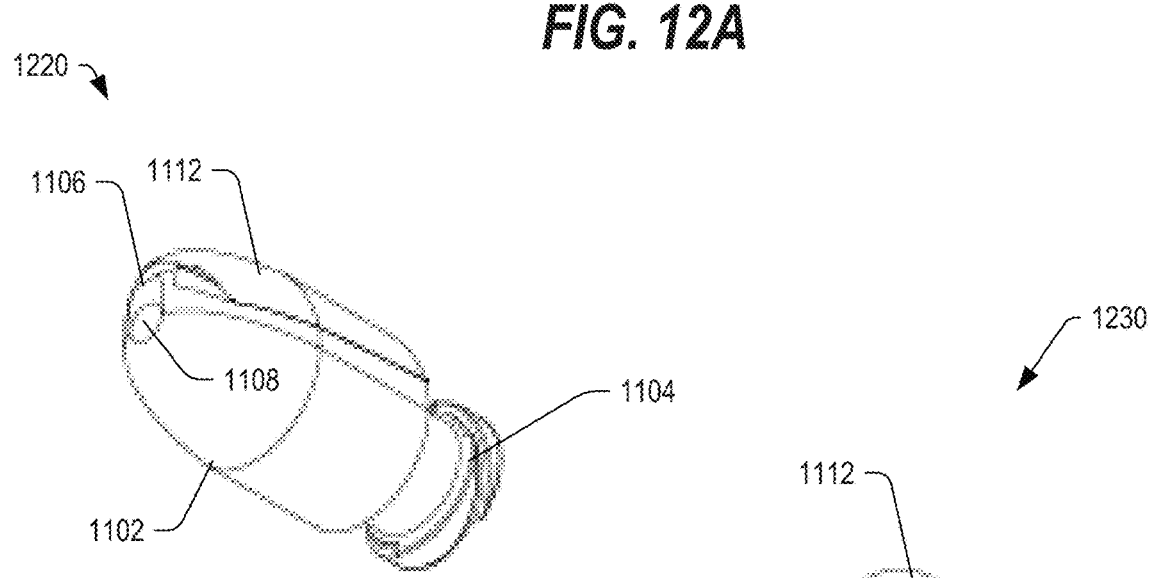
Figure 12C:
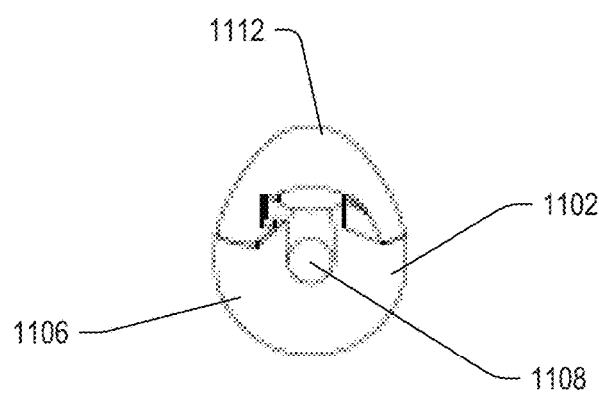

FIGS. 12A-12C depict perspective views of the second abscess draining device of FIGS. 11A-11C with the hinged fastener 1112 in a closed position, in accordance with certain embodiments of the present disclosure. In FIG. 12A, a top perspective view 1200 of the hub 1102 shows the hinged element 1112 clamped over the distal end of the tubing.

In FIG. 12B, a bottom perspective view 1220 of the hub 1102 is shown. In FIG. 12C, a front perspective view 1230 of the hub 1102 is shown. In some embodiments, the hub 1102 may be formed from a flexible, rubber or silicone material that can be compressed, bent, or otherwise deformed.

In the embodiments of FIGS. 12A-12C, the hub 1102 can be approximately the size of a pinto bean when closed. By providing a hinged element 1112 that can close to engage the distal end of the catheter tubing, the hub 1102 can facilitate the surgical procedure. By providing a small sized hub 1102, the hub 1102 can be comfortably worn after the surgery.

Figure 13A:
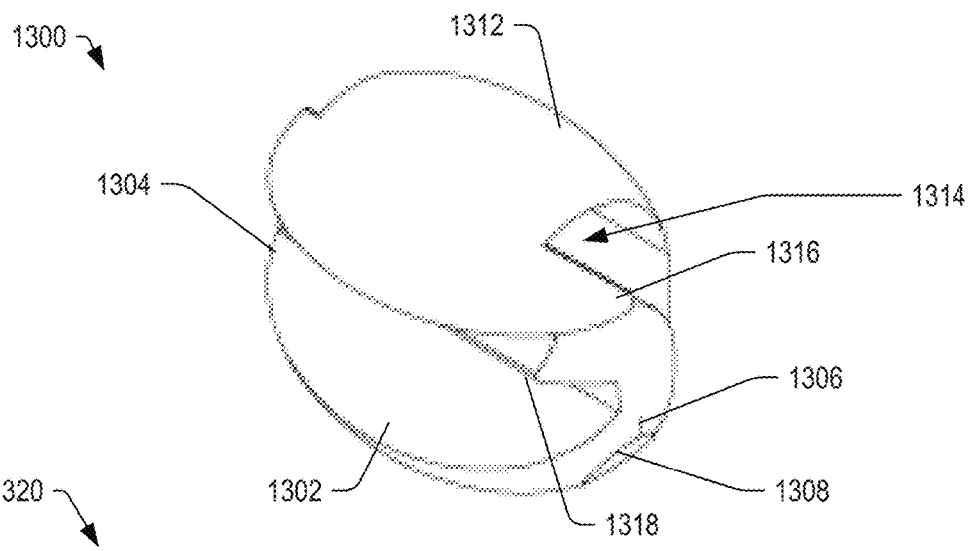
FIGS. 13A-13C depict perspective views of a third abscess draining device including a hub with a hinged fastener in an open position, in accordance with certain embodiments of the present disclosure.
Figure 13B:
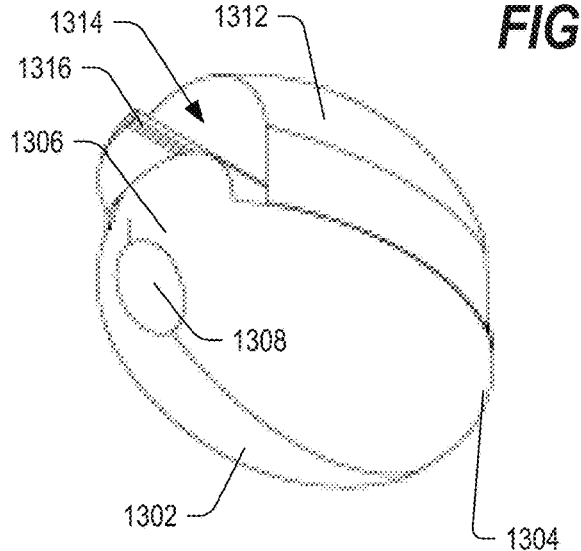
Figure 13C:
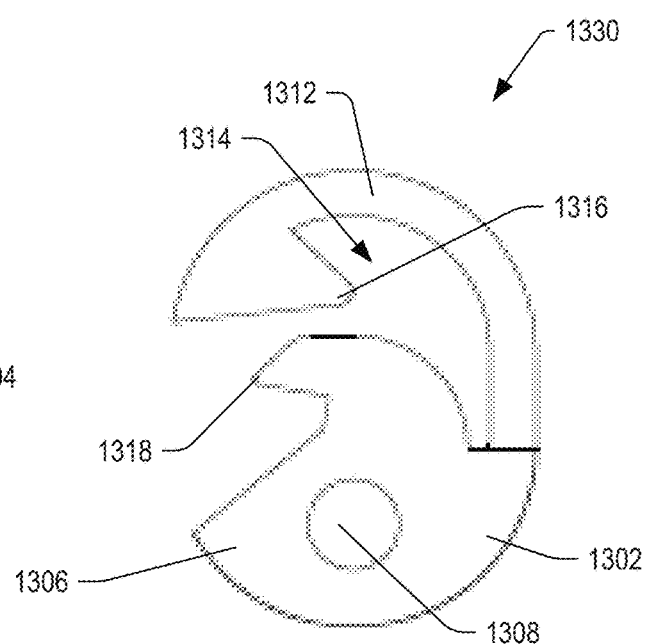

FIGS. 13A-13C depict perspective views of a third abscess draining device including a hub with a hinged fastener in an open position, in accordance with certain embodiments of the present disclosure. FIG. 13A shows a top perspective view 1300 of a hub 1302 including a proximal end 1304 and a distal end 1306. A lumen may extend from the proximal end 1304 to the distal end 1306, as represented by the opening 1308.

The hub 1302 may include a hinged fastener 1312 coupled to the hub 1302 and defining an enclosure, generally indicated at 1314. The hinged fastener 1312 may further include a fastener element 1316 configured to engage a corresponding fastener element 1318 associated with the hub 1302 to close the hinged fastener 1312 over a distal end of the catheter tubing.

In certain embodiments, a proximal end of the catheter tubing may be coupled to the opening 1308 and the distal end of the catheter tubing may extend through the skin, through the abscess and back out from the skin. The distal end may be secured by placing the distal end within the enclosure 1314 and closing the hinged fastener 1312 such that the hinged fastener 1312 can secure the distal end of the catheter tubing to the hub 1302.

FIG. 13B depicts a bottom perspective view 1320 of the hub 1302. The proximal end 1304 may include a threaded portion configured to engage a corresponding structure of the syringe or other element.

FIG. 13C illustrates a front view 1330 of the hub 1302 taken from the perspective of the distal end 1106. The fastener element 1316 is configured to engage the corresponding fastener 1318 to close the hinged element 1312 over the distal end of the tubing.

Figure 14A:
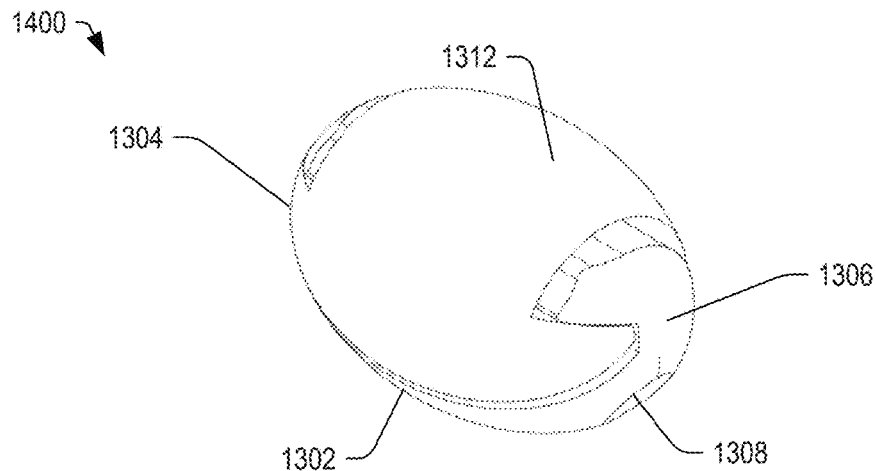
FIGS. 14A-14C depict perspective views of the third abscess draining device of FIGS. 13A-13C with the hinged fastener in a closed position, in accordance with certain embodiments of the present disclosure.
Figure 14B:
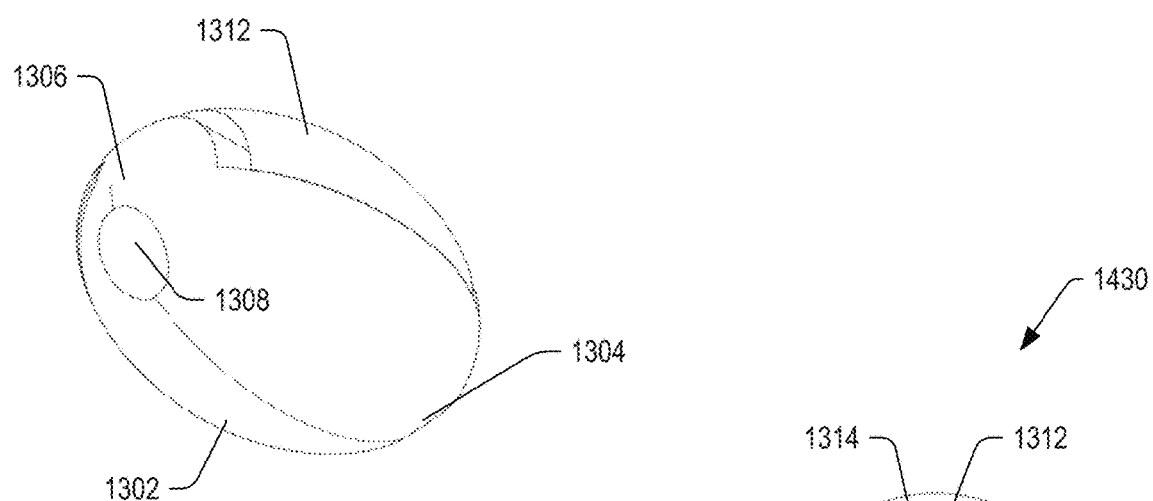
Figure 14C:
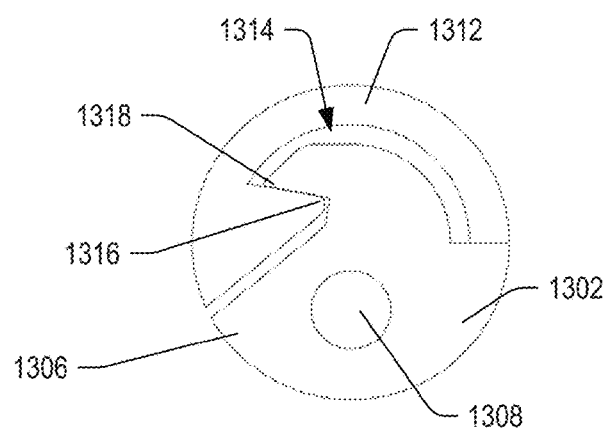

FIGS. 14A-14C depict perspective views of the second abscess draining device of FIGS. 13A-13C with the hinged fastener 1312 in a closed position, in accordance with certain embodiments of the present disclosure. In FIG. 14A, a top perspective view 1400 of the hub 1302 shows the hinged element 1312 clamped in a closed position, such as when the catheter tubing is secured by the hinged element 1312.

In FIG. 14B, a bottom perspective view 1420 of the hub 1302 is shown. In FIG. 14C, a front perspective view 1430 of the hub 1302 is shown. In some embodiments, the hub 1302 may be formed from a flexible, rubber or silicone material that can be compressed, bent, or otherwise deformed.

In the embodiments of FIGS. 14A-14C, the hub 1302 can be approximately the size of a pinto bean (or smaller) when closed. By providing a hinged element 1312 that can close to engage the distal end of the catheter tubing, the hub 1302 can facilitate the surgical procedure. By providing a small sized hub 1302, the hub 1302 can be comfortably worn after the surgery.

Figure 15A:
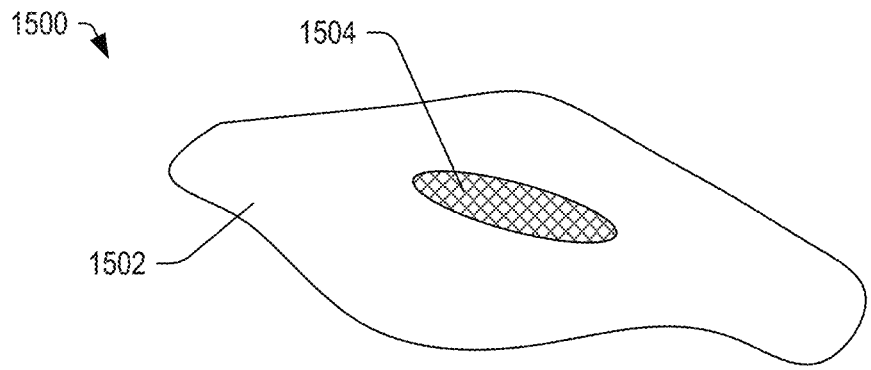
FIGS. 15A-15C illustrate a method of suturing a drainage catheter device into a wound, in accordance with certain embodiments of the present disclosure.
Figure 15B:
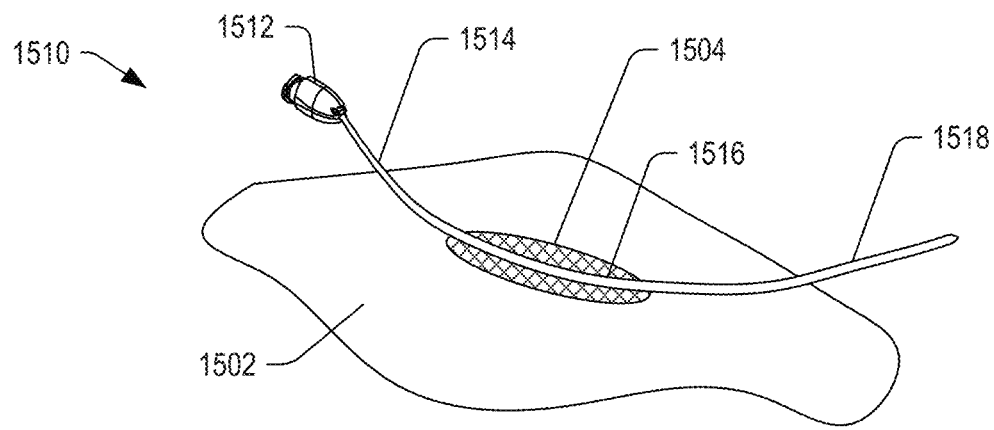
Figure 15C:
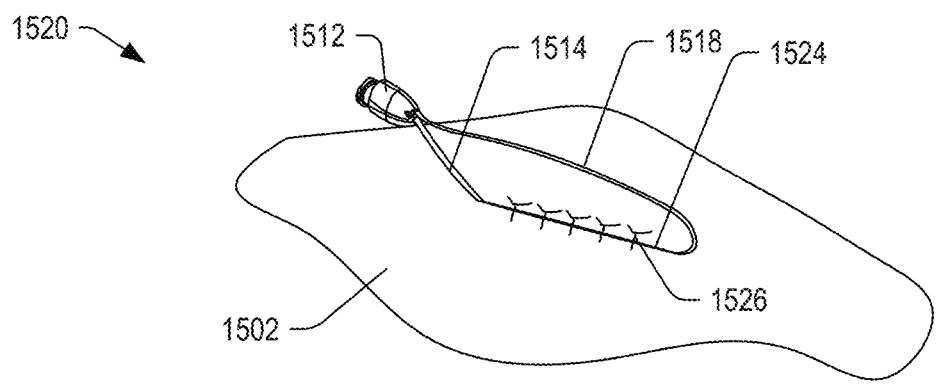

FIGS. 15A-15C illustrate a method of suturing a drainage catheter device into a wound, in accordance with certain embodiments of the present disclosure. In FIG. 15A, perspective view 1500 is shown that includes a surface 1502 including an open wound 1504 that may require sutures.

In FIG. 15B, a perspective view 1510 is shown that includes a drainage system. The drainage system may include a catheter including a proximal portion 1514, a distal portion 1518, and a portion 1516 in contact with the wound. In some embodiments, the drainage system may further include a hub 1512, which can be an embodiment of any of the hubs depicted and described with respect to any of the FIGS. 1-14C. In some embodiments, a user may select a hub 1512 (such as any of the embodiments described above) and a catheter from a plurality of available options. The catheter, for example, may include an inflatable feature, openings for irrigation, or any of the other catheter features described above. The user may then assemble the irrigation device by coupling the proximal end 1514 of the selected catheter to the selected hub 1512. The user may then position the portion 1516 in contact with the wound.

In FIG. 15C, a perspective view 1520 is shown that includes the drainage system sutured in place in the closed wound 1524 by a plurality of sutures 1526. In this example, the portion 1516 may be sown (or sutured) into the wound to facilitate drainage.

It should be appreciated that many of the examples described above assumed that a puncture element was needed to access the wound or abscess to be drained. However, some wounds may be open prior to treatment, and the drainage system may be used to drain such wounds without using a puncture element. Other embodiments are also possible.

Figure 16A:
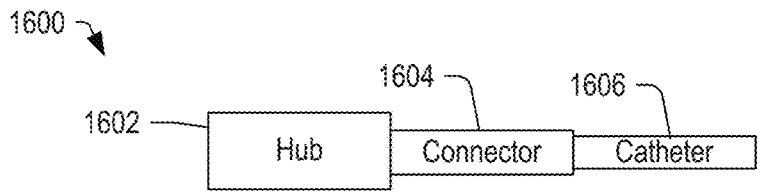
FIGS. 16A-16G depict a plurality of connectors that can be used to couple a catheter to a hub (or a catheter to a puncture device), in accordance with certain embodiments of the present disclosure.

FIGS. 16A-16G depict a plurality of connectors that can be used to couple a catheter to a hub (or a catheter to a puncture device), in accordance with certain embodiments of the present disclosure. In FIG. 16A, a block diagram 1600 of a drainage system is shown that includes a hub 1602 coupled to a catheter 1606 by a connector 1604. The connector 1604 can be a clamp connector, a strap connector, a cinch connector, a magnetic connector, a bolt/nut connector, a cinch-lock connector, a ratchet connector (such as depicted in FIGS. 2A-2C), an adhesive connector, a hook and eye connector, a buckle, a crank or winding, a loop/hook connector, a weld (mechanical or chemical) connection, a tube lock connector, or other connector. Some of the types of connectors are depicted below for ease of understanding. Further, it should be appreciated that the connector (or similar connectors) may be used to connect both the proximal and distal ends of the catheter to the hub. Some of the connector types may also be used to couple the catheter 1606 to a puncture element.

Figure 16B:
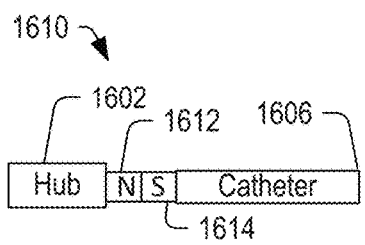

In FIG. 16B, a block diagram 1610 of a drainage system includes a hub 1602 coupled to a catheter 1606 by a magnetic coupling including a first magnet 1612 coupled to the hub 1602 and a second magnet 1614 coupled to the catheter 1606.

Figure 16C:
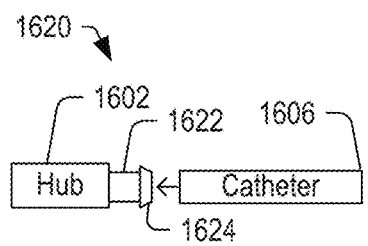

In FIG. 16C, a block diagram 1620 of a drainage system includes a hub 1602 with a connector 1622 including at least one barb 1624. The catheter 1606 may be pressed onto the connector 1622 over the barb 1624 to couple the catheter 1606 to the hub 1602.

Figure 16D:
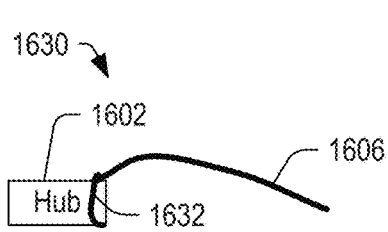

In FIG. 16D, a block diagram 1630 of a drainage system is disclosed that includes a cinch-lock type of connector 1632 configured to couple the catheter 1606 to the hub 1602.

Figure 16E:
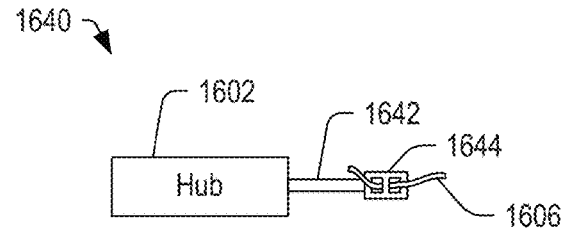

In FIG. 16E, a block diagram 1640 of a drainage system is shown that includes a buckle 1644, which may be coupled to the hub 1602 by an attachment feature 1642. In this example, the attachment feature 1642 may include a flexible strap. In an alternative embodiment, the buckle 1644 may be coupled to the hub 1602 by an adhesive or another coupling. In the illustrated example, the catheter 1606 may be coupled to the hub 1602 by weaving the end of the catheter 1606 through the buckle 1644.

Figure 16F:
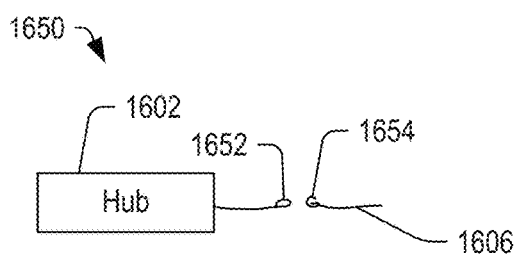

In FIG. 16F, a block diagram 1650 of a drainage system is shown that includes a loop 1652 coupled to the hub 1602 and a hook 1654 coupled to the catheter 1606. In an example, the loop 1652 and the hook 1654 may be part of a hook and eye fabric combination that can be used to secure the catheter 1606 to the hub 1602. In an alternative example, a hook 1654 may be coupled to or formed from the end of the catheter 1606 and configured to engage the loop 1652 associated with the hub 1602.

Figure 16G:
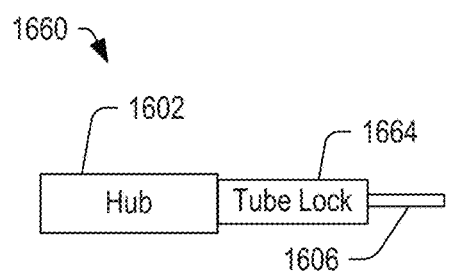

In FIG. 16G, a block diagram 1660 of a drainage system is shown that includes a tub lock 1664 coupled to the hub 1602 and configured to engage and secure an end of the catheter 1606. The tube lock 1664 may be an example of a push-to-connect type of fitting, a crimp fitting, or a shark-bite fitting that can receive and grip the catheter 1606.

While the above-examples included mechanical coupling features, it should be appreciated that the catheter 1606 may be coupled to the hub 1602 using adhesives, a mechanical (or chemical) weld, or other features. In a particular example, the catheter 1606 may be coupled to the hub 1602 by a bolt/nut combination. For example, the end of the catheter may include a nut configured to engage a threaded post or bolt of the hub 1602. In another embodiment, the catheter 1606 may include ridges or impressions configured to engage corresponding impressions or ridges in the connector 1604 of the hub 1602, securing the catheter 1606 to the hub 1602. Other embodiments are also possible.

Figure 17A:
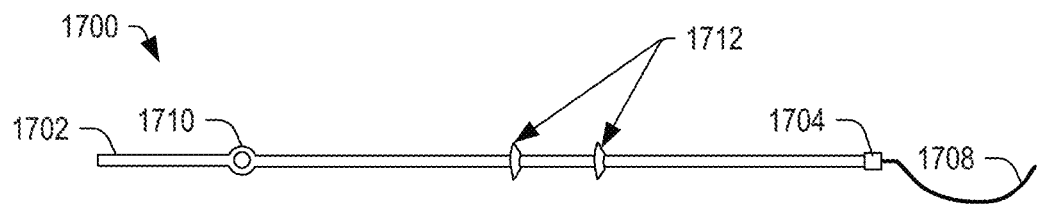
FIG. 17A depicts a drainage device including a catheter with a ring and collapsible elements configured to secure a portion of the catheter within the ring, in accordance with certain embodiments of the present disclosure.

FIG. 17A depicts a drainage device 1700 including a catheter 1702 with a ring 1710 and collapsible elements 1712 configured to secure a portion of the catheter 1702 within the ring 1710, in accordance with certain embodiments of the present disclosure. The catheter 1702 may include a proximal portion adjacent to the ring 1710 and a distal portion, which may be coupled to a curved needle 1708 by a fastening element 1704. In some embodiments, the fastening element 1704 may include a crimped portion, an adhesive, or any combination thereof.

In some embodiments, the collapsible elements 1712 may collapse when the catheter 1702 is pulled through tissue, an abscess, or the opening in the ring 1710. The collapsible element 1712 may then expand to prevent the distal end of the catheter 1702 from being pulled back through the ring 1710. In some embodiments, the ring 1710 may include a metallic element that may maintain the shape of the ring 1710. Further, if the patient were to ingest the catheter 1702 by accident, the metallic element may be detectable using X-rays or other medical procedures. Other embodiments are also possible.

Figure 17B:
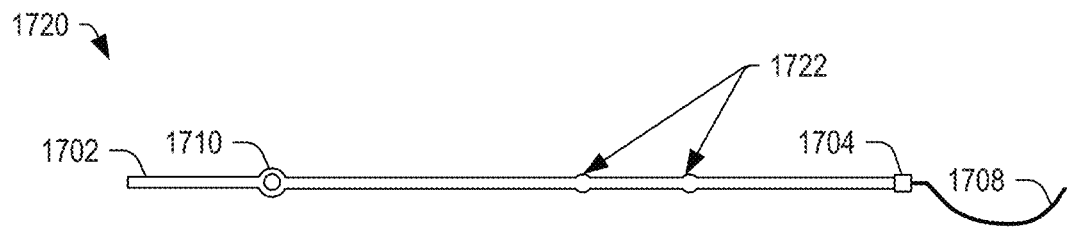
FIG. 17B depicts a drainage device including a catheter with a ring and spherical elements configured to secure a portion of the catheter within the ring, in accordance with certain embodiments of the present disclosure.

FIG. 17B depicts a drainage device 1720 including a catheter 1702 with a ring 1710 and spherical elements 1722 configured to secure a portion of the catheter 1702 within the ring 1710, in accordance with certain embodiments of the present disclosure. In this example, the spherical elements 1722 may be at least partially compressible to fit through the opening of the ring 1710 and to prevent the catheter 1702 from being pulled back through the ring 1710.

Figure 17C:
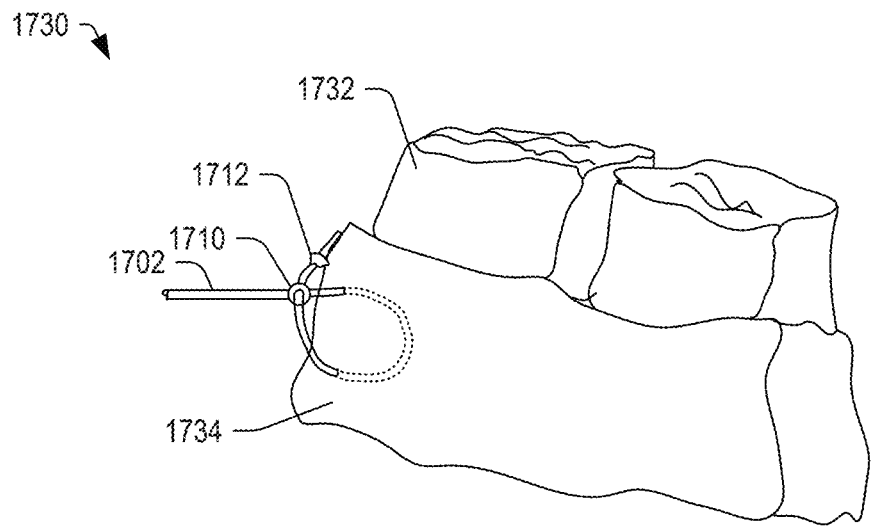
FIG. 17C depicts a diagram of a drainage device of FIG. 17A, in situ within a patient's mouth, in accordance with certain embodiments of the present disclosure.

FIG. 17C depicts a diagram 1730 of a drainage device 1700 of FIG. 17A, in situ within a patient's mouth, in accordance with certain embodiments of the present disclosure. In the illustrated example, a portion of the patient's gums 1734 and associated teeth 1732 are shown. The proximal end of the catheter 1702 and the distal end of the catheter 1702 are external to the gums 1734. A portion of the catheter 1702 (which is between the proximal and distal ends) may extend within the patient's gums. The distal end of the catheter 1702 is threaded through the opening in the ring 1710, and the collapsible element 1712 prevents the catheter 1702 from being pulled back through the ring 1710.

In this example, removal of the drainage device 1700 (or the drainage device 1720) may be accomplished by cutting the catheter 1702 between the ring 1710 and the gums 1734 and pulling the drainage device 1700. Rather than using other types of drainage devices, the drainage device 1700 enables a simple insertion and simple removal. More importantly, the small openings for insertion reduce the possibility of infection, and the simplified withdrawal procedure reduces or eliminates the need for a second surgery to remove the drainage device 1700 as compared to other drainage devices and solutions.

Figure 18:
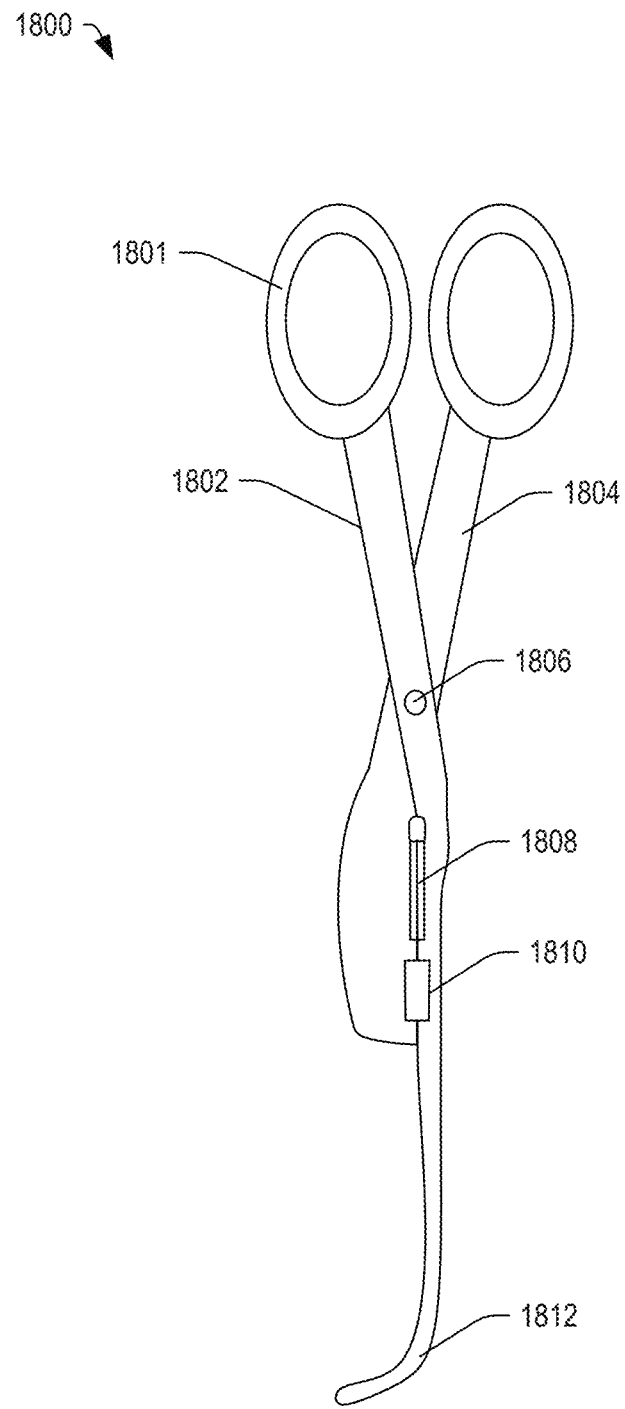
FIG. 18 depicts a diagram of a hemostat, in accordance with certain embodiments of the present disclosure.

FIG. 18 depicts a diagram of a hemostat 1800, in accordance with certain embodiments of the present disclosure. The hemostat 1800 includes handles 1801 configured to engage a user's fingers. The hemostat 1800 may further include a first arm 1802 and a second arm 1804 coupled together at a pivot location 1806 to provide a scissor/gripper function. The first arm 1802 and the second arm 1804 cooperate to provide a cutting element 1808 and a gripper element 1810. Further, the arm 1802 includes an extension 1812, which is rounded and configured to be moved around within the abscess. The extension 1812 may be curved. Further, the extension 1812 may be rounded so that the extension does not cut tissue.

In an embodiment, the physician may insert the drainage catheter and may use the gripper element 1810 to advance the catheter through the epidermis, the through the abscess. Once the distal end of the catheter is coupled to the fastener of the hub, the physician may pull on the hub to expand the opening to allow the physician to insert the extension 1812 through the same incision as the catheter. The physician may then move the extension around to help to dislodge the accumulated fluid. Other embodiments are also possible.

Figure 19:
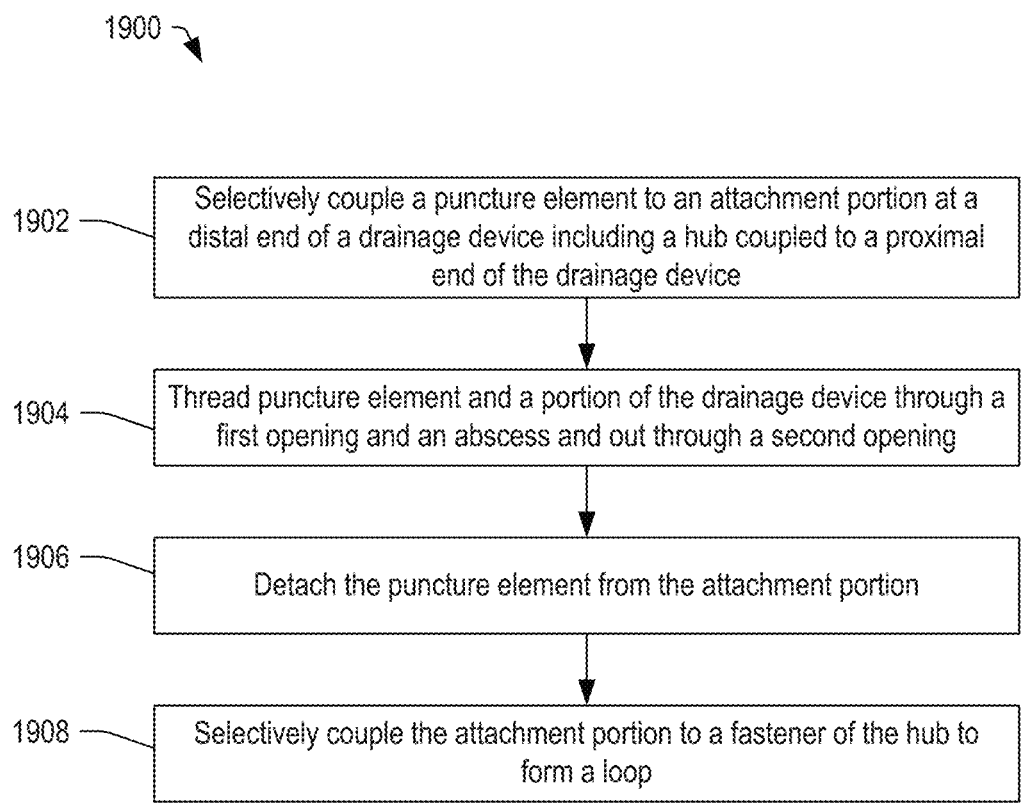
FIG. 19 depicts a diagram of a method of treating a cutaneous abscess, in accordance with certain embodiments of the present disclosure. Needle may come attached to the catheter or require attachment by the practitioner. In some embodiments the abscess cavity is irrigated after the drain is placed.

FIG. 19 depicts a diagram of a method 1900 of treating a cutaneous abscess, in accordance with certain embodiments of the present disclosure. At 1902, the method 1900 may include selectively coupling a puncture element to an attachment portion at a distal end of a drainage device that includes a hub coupled to a proximal end of the drainage device. In some embodiments, the puncture may include a puncture element and a coupling mechanism such as the third portion (or attachment portion) 136 in FIGS. 1E and 1F, which may engage a fastener element of a drainage catheter. In a particular example, the puncture element may include a first portion that includes a tip or point and that is curved or arcuate-shaped. Further, the puncture element may include a second portion including wings or protrusions having a sharpened distal edge and a blunt or smooth proximal edge. Additionally, the puncture element may include a third portion that may include one or more attachment features configured to engage and secure the catheter to the third portion. In an example, the attachment features may include an adhesive, an opening sized to receive the end of the catheter, hooks (ridges or teeth) configured to mechanically grip the end of the catheter, other attachment features, or any combination thereof. In one particular example, the end of the catheter may be inserted into an opening of the third portion of the puncture element, and the third portion may be crimped or bent to mechanically secure the puncture element to the catheter. In still another possible embodiment, the third portion may include an opening (similar to the eye of a needle) through which the catheter may be threaded to secure the catheter to the puncture element. Other embodiments are also possible.

At 1904, the method 1900 may include threading the puncture element and the drainage device through a first opening and an abscess and out through a second opening. In an embodiment, the drainage device may include a catheter that may be attached to the puncture element and drawn through the epidermis, through the abscess, and back through the epidermis. The puncture element may include a tip or point, a curved portion, an expander portion that includes one or more blades extending laterally to expand the opening created by the tip. In some embodiments, a portion of the catheter may include openings, a balloon, or both, which may be positioned within the abscess.

At 1906, the method 1900 may include detaching the puncture element from the attachment portion. In an example, the puncture element may be detached by cutting through a cut area provided in the attachment portion or by cutting the catheter at a location adjacent to the puncture element. At 1908, the method 1900 may include selectively coupling the attachment portion to a fastener of the hub to form a loop. In some embodiments, the fastener and the attachment portion may cooperate to form a zip-tie type of attachment. In other embodiments, the attachment portion may include a clip or fastener that may be closed over the catheter to secure the distal end of the catheter and to hold the catheter in a loop shape. In some embodiments, the fastener may extend through at least a portion of the hub. Further, in some embodiments, the hub may include an irrigation port, a pressurized fluid port, or both. Other embodiments are also possible.

In conjunction with the devices described above with respect to FIGS. 1A-17C and 19, a drainage device is disclosed that includes a hub and a catheter having a proximal end coupled to the hub. The hub may include a fastener configured to engage a distal end of the catheter to form a loop that extends through a first incision in the epidermis, through an abscess or other structure to be drained, and back through a second incision in the epidermis. The fastener may be a zip-tie fastener, cinch lock, a clip, a latch, a knot, a magnet, a barbed or double barbed attachment, glue/adhesive/cement, chemical bond/weld, double hinge clamp, intermediate material bond, ratchet, Velcro, buckle, carabiner, spring loaded clamp, directional clamp, swage, tube lock, "push to connect" tube fitting, crimp fitting, shark bite fitting, tape or another type of fastener configured to engage and secure the distal end of the catheter.

In some embodiments, the hub may include an irrigation port to receive a sterile irrigation fluid and the catheter may include a lumen extending from the irrigation port to openings in the catheter. In some embodiments, the openings may be positioned within a treatment area to deliver the irrigation fluid. In some embodiments, the hub may include a pressurized fluid port and the catheter may include a pressurized fluid lumen extending from the pressurized fluid port to a balloon.

Further, in conjunction with the hemostat of FIG. 18, a tool is described that may be used in conjunction with the drainage devices of FIGS. 1A-17C and 19. In an example, the hemostat may include a gripping element configured to engage a needle or puncture element to guide the puncture element and the attached catheter through the epidermis and the abscess. Further, once the puncture element is pushed back through a second incision of the epidermis, the physician may utilize the cutting element of the hemostat to cut off the puncture element. The hemostat may be used to cut portions of the faster element and an extension element of the hemostat may be inserted through one of the incisions and moved around to facilitate the treatment.

While the above discussion has focused on implementations of the drainage catheter system used with abscesses, the drainage catheter systems and embodiments described above may be used with other drainage situations including, but not limited to plastic surgery, breast surgery (to prevent collection of blood, lymph fluid, or both), orthopedic procedures, chest drainage, infected cysts, pancreatic surgery (to drain secretions), biliary surgery, thyroid surgery, neurosurgery (to remediate risk of intracranial pressure), urinary catheters, nasogastric tubes, and other procedures. In some embodiments, such as oral surgery, the hub may be smaller in order to reduce irritation. In other embodiments, the hub may be larger in order to facilitate access to fluid ports. Other embodiments are also possible.

Although the present invention has been described with reference to preferred embodiments, workers skilled in the art will recognize that changes may be made in form and detail without departing from the scope of the invention.

What is claimed is:

1. An apparatus comprising:
a hub including a hub channel;
a flexible conduit coupled to the hub; and
a blade coupled to the conduit;
wherein: (a)(i) the hub channel is coupled to a first portion of the conduit; and (a)(ii) the first portion of the conduit is hollow;
wherein: (b)(i) in a first configuration the conduit and the hub couple to each other in a non-loop orientation; (b)(ii) in a second configuration the conduit and the hub couple to each other in a loop orientation, the loop orientation including a loop having a circumference; (b)(iii) in a third configuration the conduit and the hub couple to each other in an additional loop orientation, the additional loop orientation including an additional loop having an additional circumference; (b)(iv) the additional circumference is smaller than the circumference;
wherein: (c)(i) the first portion of the conduit includes a first aperture, the first aperture to fluidly couple an external irrigation source to the conduit via the hub channel; (c)(ii) a second portion of the conduit includes at least one second aperture in a sidewall of the conduit; (c)(iii) the conduit includes a lumen that couples the first aperture to the at least one second aperture; (c)(iv) a third portion of the conduit is coupled to the blade; and (c)(v) the second portion of the conduit is between the first and third portions of the conduit;
wherein: (d)(i) in the first configuration the first portion of the conduit couples to the hub and the third portion of the conduit does not directly contact the hub; (d)(ii) in both of the second and third configurations the third portion of the conduit directly contacts the hub; (d)(iii) the first, second, and third portions of the conduit collectively include the lumen; (d)(iv) the lumen is open in the first portion of the conduit; (d)(v) in each of the first, second, and third configurations the lumen is open in the third portion of the conduit; and (d)(vi) in a fourth configuration the hub seals the lumen and the lumen is closed in the third portion of the conduit.

2. The apparatus of claim 1 wherein:
the blade includes: (a)(i) a long axis along a length of the blade, and (a)(ii) a short axis that is orthogonal to the long axis;
the blade comprises: (b)(i) a first blade portion including a first width measured parallel to the short axis, and (b)(ii) a second blade portion including a second width measured parallel to the short axis;
the first blade portion is between the third portion of the conduit and the second blade portion;
the first width is greater than the second width.

3. The apparatus of claim 2 wherein:
the blade includes a third blade portion;
the second blade portion is between the first and third blade portions;
the third blade portion is curved in a plane, the plane being parallel to the long axis.

4. The apparatus of claim 3 wherein the second blade portion includes at least one cutting edge.

5. The apparatus of claim 4 wherein the second blade portion includes two cutting edges that are not contiguous with one another.

6. The apparatus of claim 5 wherein each of the two cutting edges taper outwardly as each of the two cutting edges progresses toward the third portion of the conduit.

7. The apparatus of claim 6 wherein:
the third blade portion does not include the two cutting edges;
each of the two cutting edges taper outwardly as each of the two cutting edges progresses away from the third blade portion.

8. The apparatus of claim 7 wherein:
the third blade portion comprises more than 50% of an overall length of the blade;
a majority of the third blade portion is not tapered.

9. The apparatus of claim 1 wherein in the fourth configuration the hub compresses the third portion of the conduit to narrow the lumen in the third portion of the conduit.

10. The apparatus of claim 9 wherein the hub includes a lock to lock the third portion of the conduit to the hub.

11. The apparatus of claim 9 wherein:
the hub includes an additional channel to receive the third portion of the conduit;
a sub-portion of the third portion of the conduit directly contacts the additional channel in the second configuration;
another sub-portion of the third portion of the conduit directly contacts the additional channel in the third configuration;
the additional channel extends from one side of the hub to another side of the hub.

12. The apparatus of claim 9 wherein in the fourth configuration the hub is configured to simultaneously compress the third portion of the conduit to narrow the lumen while communicating irrigating fluid from the hub channel to the at least one second aperture in the sidewall of the conduit.

* * * * *